(12) United States Patent
Carley

(10) Patent No.: US 8,758,398 B2
(45) Date of Patent: Jun. 24, 2014

(54) APPARATUS AND METHOD FOR DELIVERING A CLOSURE ELEMENT

(75) Inventor: Michael T. Carley, San Jose, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 487 days.

(21) Appl. No.: 11/852,190

(22) Filed: Sep. 7, 2007

(65) Prior Publication Data

US 2008/0065152 A1    Mar. 13, 2008

Related U.S. Application Data

(60) Provisional application No. 60/843,325, filed on Sep. 8, 2006.

(51) Int. Cl.
*A61B 17/08* (2006.01)
*A61B 17/10* (2006.01)

(52) U.S. Cl.
USPC .......................................... 606/213; 606/142

(58) Field of Classification Search
USPC ......... 606/232, 153, 213, 151, 142, 139, 143, 606/216, 215
See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 556,082 A | 3/1896 | Boeddinghaus |
| 1,088,393 A | 2/1914 | Backus |
| 1,242,139 A | 10/1917 | Callahan |
| 1,331,401 A | 2/1920 | Summers |
| 1,480,935 A | 1/1924 | Gleason |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

U.S. Appl. No. 61/015,144, filed Dec. 19, 2007, Mackiewicz et al.

(Continued)

*Primary Examiner* — Tuan V Nguyen
(74) *Attorney, Agent, or Firm* — Workman Nydegger; Randy Shen

(57) ABSTRACT

An apparatus for delivering and deploying a closure element to an opening formed in a body lumen, including a delivery assembly positionable through the tissue and into the opening. The delivery assembly includes a distal locator portion and a carrier assembly oriented proximal to the distal locator portion. The distal locator portion is configured to selectably engage the body lumen adjacent to the opening, and the carrier assembly is configured to carry and support the closure element in a substantially tubular configuration. The carrier assembly is further configured to urge the closure element toward an expanded cross-sectional dimension for deployment thereof, such that the closure element is oriented to engage the tissue when deployed and, when released, to return to the natural, substantially planar configuration and the natural cross-section dimension wherein the engaged tissue is drawn substantially closed.

11 Claims, 18 Drawing Sheets

(56) References Cited

U.S. PATENT DOCUMENTS

| | | |
|---|---|---|
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,029,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |

(56) References Cited

U.S. PATENT DOCUMENTS

| | | |
|---|---|---|
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Lindon et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,709,224 A | 1/1998 | Behl et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |

(56) References Cited

U.S. PATENT DOCUMENTS

| | | |
|---|---|---|
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A * | 7/1998 | Cragg et al. .................. 606/216 |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A * | 3/2000 | Lee .................................. 606/213 |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,513 A | 9/2000 | Bailey et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |

(56) References Cited

U.S. PATENT DOCUMENTS

| | | |
|---|---|---|
| 6,210,407 B1 | 4/2001 | Webster |
| 6,220,248 B1 | 4/2001 | Voegele et al. |
| 6,221,102 B1 | 4/2001 | Baker et al. |
| 6,231,561 B1 | 5/2001 | Frazier et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,645,255 B2 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B2 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |

(56) References Cited

U.S. PATENT DOCUMENTS

| | | |
|---|---|---|
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,727,249 B2 | 6/2010 | Rahmani |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelöv |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026208 A1 | 2/2002 | Belef |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0062104 A1 | 5/2002 | Ashby et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0193808 A1 | 12/2002 | Belef et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |

(56) References Cited

U.S. PATENT DOCUMENTS

| | | |
|---|---|---|
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083230 A1 | 4/2007 | Javois |
| 2007/0083231 A1 | 4/2007 | Lee |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2011/0270282 A1 | 11/2011 | Lemke |
| 2012/0035630 A1 | 2/2012 | Roorda |
| 2012/0245603 A1 | 9/2012 | Voss |
| 2012/0245623 A1 | 9/2012 | Karineimi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |

FOREIGN PATENT DOCUMENTS

| | | |
|---|---|---|
| DE | 197 11 288 | 1/1998 |
| DE | 297 23 736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |

(56) References Cited

FOREIGN PATENT DOCUMENTS

| | | |
|---|---|---|
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0452 | 12/2002 |
| IE | S 2002/0664 | 2/2003 |
| IE | S 2002/0665 | 2/2003 |
| IE | S 2002/0451 | 7/2003 |
| IE | S 2002/0552 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | PCT/US07/78051 | 9/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 20010527 | 1/2001 |
| ZA | 200100528 | 1/2001 |

OTHER PUBLICATIONS

U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson et al.
U.S. Appl. No. 09/610,128, filed Jul. 5, 2000, Kerievsky.
U.S. Appl. No. 09/866,551, filed May 25, 2001, Ginn.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/006,400, Aug. 2, 2010, Notice of Allowance.
U.S. Appl. No. 10/517,004, Aug. 3, 2010, Notice of Allowance.
U.S. Appl. No. 10/541,083, Aug. 17, 2010, Notice of Allowance.
U.S. Appl. No. 10/638,115, Aug. 13, 2010, Notice of Allowance.
U.S. Appl. No. 10/682,459, Apr. 28, 2010, Office Action.
U.S. Appl. No. 10/787,073, Aug. 25, 2010, Notice of Allowance.
U.S. Appl. No. 11/048,503, Jul. 30, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.

(56) References Cited

OTHER PUBLICATIONS

U.S. Appl. No. 11/427,309, Nov. 6, 2009, Office Action.
U.S. Appl. No. 11/427,309, Apr. 26, 2010, Office Action.
U.S. Appl. No. 11/508,656, Aug. 30, 2010, Office Action.
U.S. Appl. No. 11/675,462, Aug. 31, 2010, Office Action.
U.S. Appl. No. 11/757,108, Nov. 25, 2009, Office Action.
U.S. Appl. No. 11/958,281, Sep. 2, 2010, Office Action.
U.S. Appl. No. 11/959,334, Jul. 23, 2010, Notice of Allowance.
U.S. Appl. No. 12/403,256, Aug. 19, 2010, Notice of Allowance.
U.S. Appl. No. 10/616,832, Sep. 20, 2010, Notice of Allowance.
U.S. Appl. No. 10/787,073, Sep. 15, 2010, Issue Notification.
U.S. Appl. No. 11/152,562, Sep. 16, 2010, Notice of Allowance.
U.S. Appl. No. 11/427,297, Sep. 15, 2010, Office Action.
U.S. Appl. No. 11/767,818, Sep. 30, 2010, Office Action.
U.S. Appl. No. 12/365,397, Sep. 13, 2010, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/097,072, filed Sep. 15, 2008, Sibbitt, Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/481,377, filed Jun. 9, 2009, Clark.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery

(56) References Cited

OTHER PUBLICATIONS

1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001 Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.

(56) References Cited

OTHER PUBLICATIONS

U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/744,089, Nov. 26, 2008, Office Action.
U.S. Appl. No. 11/744,089, Aug. 14, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,277, Jul. 8, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 09/866,551, filed May 25, 2001.
U.S. Appl. No. 11/396,141, filed Mar. 31. 2006.
U.S. Appl. No. 11,675,462, filed Feb. 15, 2007.
U.S. Appl. No. 11/744,089, filed May 3, 2007.
Database WPI; Section PQ, Week 200120; Derwent Publications Ltd., London GB; AN 2001-203165; XP002199926 & ZA 200 100 528 A (Anthony T), Feb. 28, 2001 abstract.
"Hand tool for forming telephone connections—comprises pliers with reciprocably driven ram crimping clip around conductors against anvil", Derwant-ACC—No. 1978-B8090A.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/682,459, May 12, 2010, Office Action.
U.S. Appl. No. 11/406,203, Oct. 6, 2010, Issue Notification.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 11/508,715, Oct. 18, 2010, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/966,923, filed Dec. 13, 2010, Cummins et al.

(56) References Cited

OTHER PUBLICATIONS

U.S. Appl. No. 12/973,204, filed Dec. 20, 2010, Jabba et al.
U.S. Appl. No. 12/987,792, filed Jan. 10, 2011, Palermo et al.
U.S. Appl. No. 10/147,774, Dec. 2, 2010, Notice of Allowance.
U.S. Appl. No. 10/435,104, Jan. 12, 2011, Issue Notification.
U.S. Appl. No. 10/517,004, Nov. 23, 2010, Issue Notification.
U.S. Appl. No. 10/541,083, Dec. 1, 2010, Issue Notification.
U.S. Appl. No. 10/638,115, Dec. 22, 2010, Issue Notification.
U.S. Appl. No. 11/048,503, Dec. 8, 2010, Issue Notification.
U.S. Appl. No. 11/113,549, Jan. 4, 2011, Office Action.
U.S. Appl. No. 11/198,811, Oct. 20, 2010, Issue Notification.
U.S. Appl. No. 11/427,309, Nov. 15, 2010, Office Action.
U.S. Appl. No. 11/959,334, Nov. 10, 2010, Issue Notification.
U.S. Appl. No. 12/106,928, Oct. 25, 2010, Office Action.
U.S. Appl. No. 12/113,851, Dec. 16, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Jan. 24, 2011, Office Action.
U.S. Appl. No. 12/403,256, Nov. 23, 2010, Issue Notification.
U.S. Appl. No. 12/945,646, Jan. 20, 2011, Office Action.
U.S. Appl. No. 11/344,891, Jan. 22, 2013, Notice of Allowance.
U.S. Appl. No. 12/961,331, Feb. 1, 2013, Office Action.
U.S. Appl. No. 13/030,922, Jan. 31, 2013, Office Action.
U.S. Appl. No. 13/153,594, Jan. 29, 2013, Office Action.
U.S. Appl. No. 13/615,547, Jan. 18, 2013, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 13/488,233, Feb. 5, 2013, Notice of Allowance.
U.S. Appl. No. 10/667,144, Feb. 15, 2012, Issue Notification.
U.S. Appl. No. 12/135,858, Feb. 16, 2012, Office Action.
U.S. Appl. No. 12/608,769, Feb. 10, 2012, Office Action.
U.S. Appl. No. 12/684,400, Feb. 13, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/945,646, Feb. 21, 2012, Notice of Allowance.
U.S. Appl. No. 12/114,091, Apr. 5, 2012, Office Action.
U.S. Appl. No. 12/684,542, Apr. 16, 2012, Office Action.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 12/338,977, Jan. 19, 2012, Office Action.
U.S. Appl. No. 12/684,569, Jan. 27, 2012, Office Action.
U.S. Appl. No. 12/113,851, Mar. 29, 2012, Office Action.
U.S. Appl. No. 12/403,277, Apr. 3, 2012, Office Action.
U.S. Appl. No. 13/308,227, filed Nov. 30, 2011, Yibarren.
U.S. Appl. No. 12/688,065, Apr. 26, 2012, Office Action.
U.S. Appl. No. 13/028,041, filed Feb. 15, 2011, Von Oepen.
U.S. Appl. No. 13/030,922, filed Feb. 18, 2011, Cummins.
U.S. Appl. No. 13/039,087, filed Mar. 2, 2011, Palermo et al.
U.S. Appl. No. 13/112,618, filed May 20, 2011, Gianotti et al.
U.S. Appl. No. 13/112,631, filed May 20, 2011, Voss.
U.S. Appl. No. 10/682,459, Apr. 1, 2011, Notice of Allowance.
U.S. Appl. No. 11/396,731, Mar. 22, 2011, Office Action.
U.S. Appl. No. 11/427,297, Mar. 21, 2011, Office Action.
U.S. Appl. No. 11/958,281, Mar. 10, 2011, Office Action.
U.S. Appl. No. 12/113,851, Apr. 27, 2011, Office Action.
U.S. Appl. No. 12/114,031, May 11, 2011, Office Action.
U.S. Appl. No. 12/122,603, Mar. 3, 2011, Office Action.
U.S. Appl. No. 12/122,603, Apr. 22, 2011, Office Action.
U.S. Appl. No. 12/143,020, May 11, 2011, Restriction Requirement.
U.S. Appl. No. 12/403,277, Mar. 31, 2011, Office Action.
U.S. Appl. No. 12/481,377, Apr. 28, 2011, Restriction Requirement.
U.S. Appl. No. 12/955,859, May 26, 2011, Restriction Requirement.
U.S. Appl. No. 10/667,144, Oct. 28, 2011, Notice of Allowance.
U.S. Appl. No. 12/945,646, Oct. 26, 2011, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 12/393,877, Dec. 13, 2011, Office Action.
U.S. Appl. No. 12/941,809, Dec. 13, 2011, Restriction Requirement.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/955,859, Dec. 15, 2011. Office Action.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 12/402,398, Mar. 13, 2013, Notice of Allowance.
U.S. Appl. No. 13/028,041, Jan. 4, 2013, Office Action.
U.S. Appl. No. 13/028,041, Feb. 26, 2013, Office Action.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 10/682,459, Aug. 10, 2011, Issue Notification.
U.S. Appl. No. 11/396,731, Sep. 1, 2011, Office Action.
U.S. Appl. No. 12/608,773, Jun. 7, 2012, Office Action.
U.S. Appl. No. 13/026,989, Jun. 8, 2012, Office Action.
U.S. Appl. No. 12/481,377, Jun. 21, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Aug. 3, 2011, Office Action.
U.S. Appl. No. 12/114,031, Aug. 2, 2011, Office Action.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/122,603, Sep. 23, 2011, Office Action.
U.S. Appl. No. 12/393,877, Sep. 29, 2011, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.

(56) References Cited

OTHER PUBLICATIONS

U.S. Appl. No. 12/987,792, Sep. 17, 2012, Office Action.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/675,462, Dec. 22, 2011, Notice of Allowance.
U.S. Appl. No. 12/135,858, Jul. 13, 2011, Office Action.
U.S. Appl. No. 12/955,859, Jul. 21, 2011, Office Action.
U.S. Appl. No. 13/026,989, Sep. 16, 2011, Office Action.
U.S. Appl. No. 12/608,773, Jan. 7, 2013, Office Action.
U.S. Appl. No. 13/490,143, Jan. 4, 2013, Office Action.
U.S. Appl. No. 12/897,358, Jan. 12, 2012, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 13/026,989, Aug. 23, 2013, Office Action.
U.S. Appl. No. 13/308,227, Sep. 11, 2013, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 13/898,202, filed May 20, 2013, Walberg et al.
U.S. Appl. No. 10/786,444, Jul. 11, 2013, Notice of Allowance.
U.S. Appl. No. 10/908,721, Jul. 18, 2013, Notice of Allowance.
U.S. Appl. No. 11/396,141, Apr. 30, 2013, Office Action.
U.S. Appl. No. 11/427,309, Jun. 7, 2013, Notice of Allowance.
U.S. Appl. No. 11/532,325, Jul. 17, 2013, Office Action.
U.S. Appl. No. 11/744,089, Apr. 15, 2013, Office Action.
U.S. Appl. No. 12/106,928, Jun. 28, 2013, Office Action.
U.S. Appl. No. 12/106,937, Jun. 28, 2013, Office Action.
U.S. Appl. No. 12/338,977, Jun. 19, 2013, Office Action.
U.S. Appl. No. 12/848,642, Apr. 26, 2013, Office Action.
U.S. Appl. No. 12/850,242, Apr. 18, 2013, Office Action.
U.S. Appl. No. 12/941,809, Jul. 3, 2013, Office Action.
U.S. Appl. No. 12/955,859, May 16, 2013, Office Action.
U.S. Appl. No. 12/961,331, Jul. 3, 2013, Office Action.
U.S. Appl. No. 13/030,922, Jul. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/112,618, Jun. 7, 2013, Office Action.
U.S. Appl. No. 13/112,631, Jun. 26, 2013, Office Action.
U.S. Appl. No. 13/153,594, May 29, 2013, Office Action.
U.S. Appl. No. 13/490,143, Apr. 29, 2013, Notice of Allowance.
U.S. Appl. No. 13/525,839, Jul. 15, 2013, Notice of Allowance.
U.S. Appl. No. 13/615,547, Apr. 12, 2013, Notice of Allowance.
U.S. Appl. No. 13/615,547, Jul. 10, 2013, Issue Notification.
U.S. Appl. No. 13/791,829, May 29, 2013, Office Action.
U.S. Appl. No. 12/114,091, Jul. 7, 2011, Office Action.
U.S. Appl. No. 12/945,646, Jul. 6, 2011, Office Action.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, filed Feb. 16, 2011, Issue Notification.
U.S. Appl. No. 11/767,818, filed Feb. 16, 2011, Office Action.
U.S. Appl. No. 11/396,141, Aug. 21, 2013, Office Action.
U.S. Appl. No. 13/028,041, Aug. 21, 2013, Notice of Allowance.
U.S. Appl. No. 13/490,143, Aug. 21, 2013, Issue Notification.
U.S. Appl. No. 10/908,721, Nov. 6, 2013, Issue Notification.
U.S. Appl. No. 11/396,141, Nov. 4, 2013, Notice of Allowance.
U.S. Appl. No. 11/411,925, Oct. 1, 2013, Office Action.
U.S. Appl. No. 11/744,089, Nov. 20, 2013, Issue Notification.
U.S. Appl. No. 12/122,603, Nov. 20, 2013, Office Action.
U.S. Appl. No. 12/688,065, Oct. 18, 2013, Office Action.
U.S. Appl. No. 12/850,242, Nov. 20, 2013, Issue Notification.
U.S. Appl. No. 12/941,809, Nov. 8, 2013, Office Action.
U.S. Appl. No. 12/955,859, Nov. 13, 2013, Issue Notification.
U.S. Appl. No. 12/961,331, Sep. 20, 2013, Advisory Action.
U.S. Appl. No. 13/052,634, Nov. 8, 2013, Office Action.
U.S. Appl. No. 13/112,618, Nov. 20, 2013, Office Action.
U.S. Appl. No. 13/153,594, Oct. 16, 2013, Notice of Allowance.
U.S. Appl. No. 13/791,829, Oct. 8, 2013, Notice of Allowance.
U.S. Appl. No. 11/113,549, Mar. 14, 2014, Notice of Allowance.
U.S. Appl. No. 11/396,141, Mar. 19, 2014, Issue Notification.
U.S. Appl. No. 11/411,925, Feb. 5, 2014, Notice of Allowance.
U.S. Appl. No. 12/106,937, Jan. 22, 2014, Office Action.
U.S. Appl. No. 12/848,642, Feb. 3, 2014, Notice of Allowance.
U.S. Appl. No. 12/941,809, Feb. 3, 2014, Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/222,899, Jan. 10, 2014, Office Action.
U.S. Appl. No. 13/898,202 Jan. 3, 2014, Office Action.

* cited by examiner

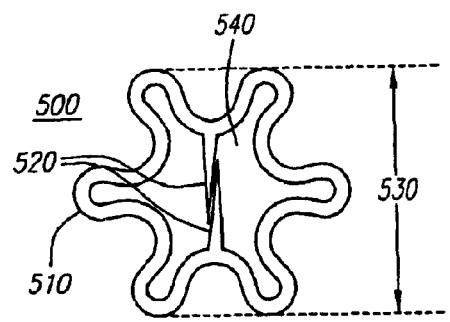
FIG._3A
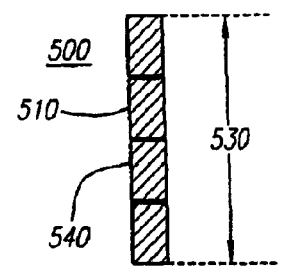
FIG._3B
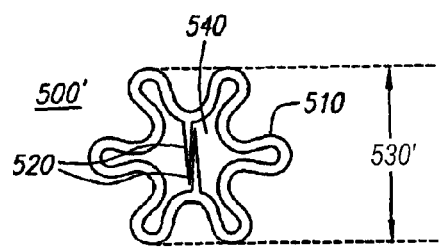
FIG._3C
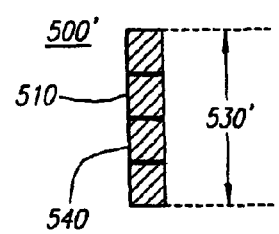
FIG._3D
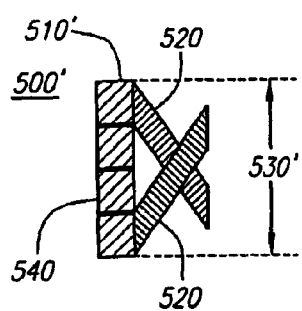
FIG._3E
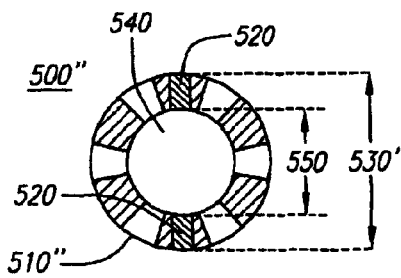
FIG._3F
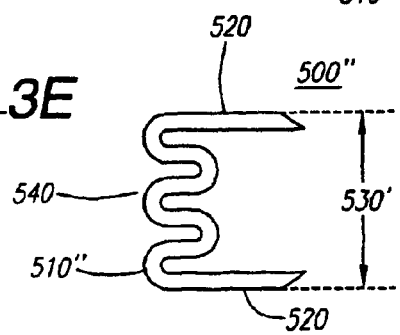
FIG._3G

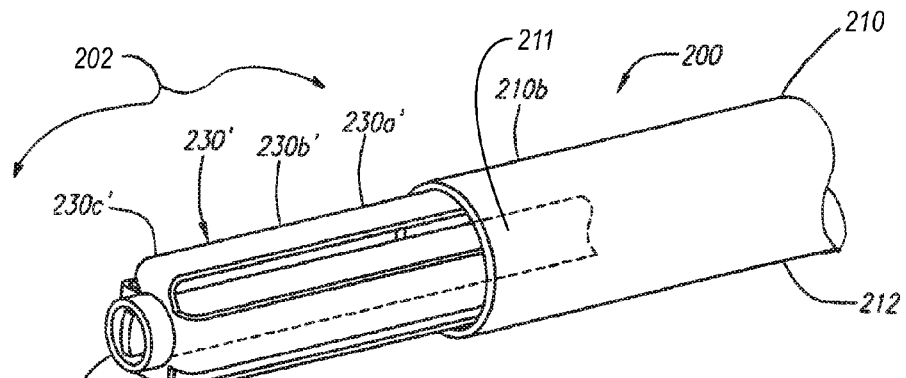
FIG._4A
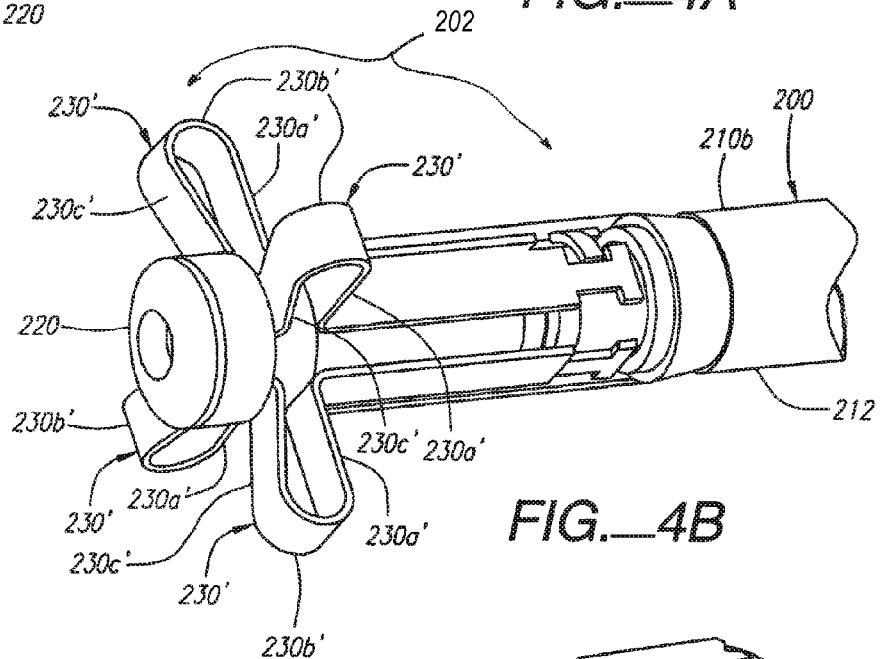
FIG._4B
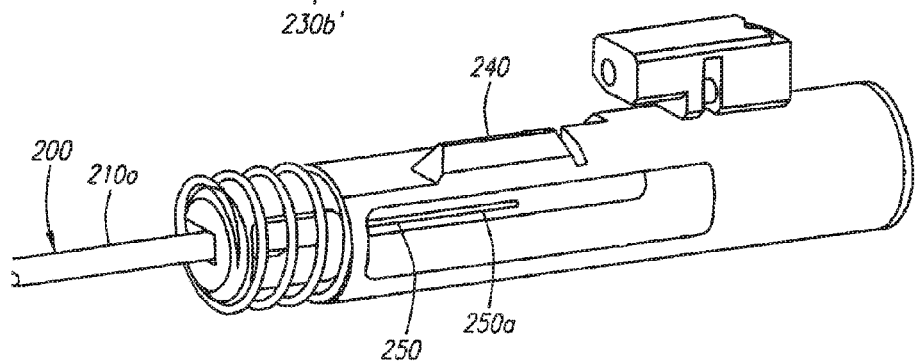
FIG._4C

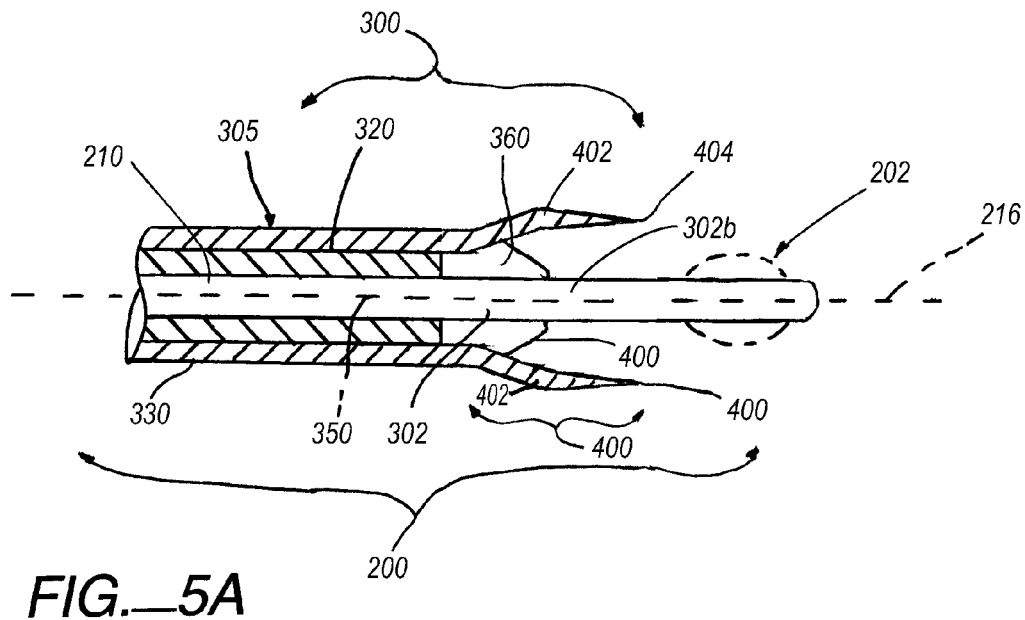
FIG._5A
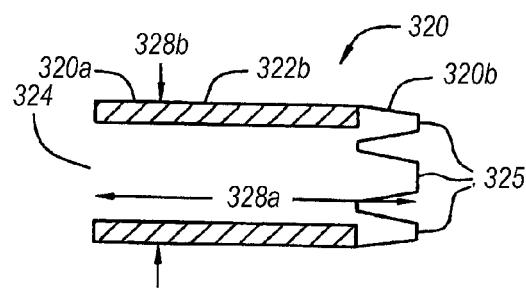
FIG._5B
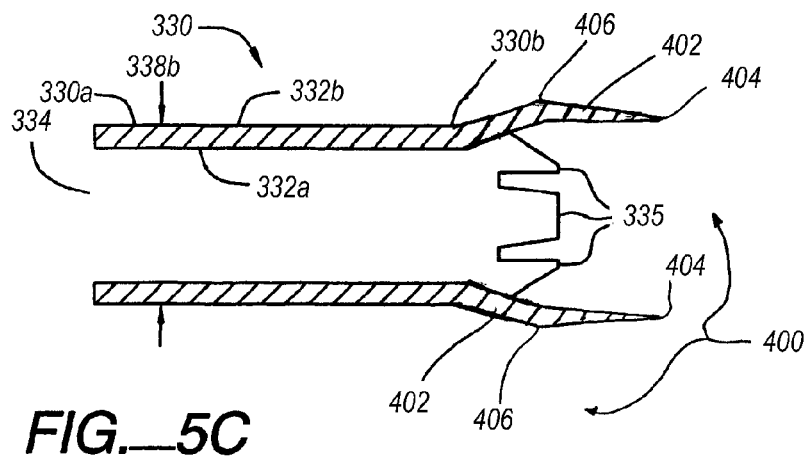
FIG._5C

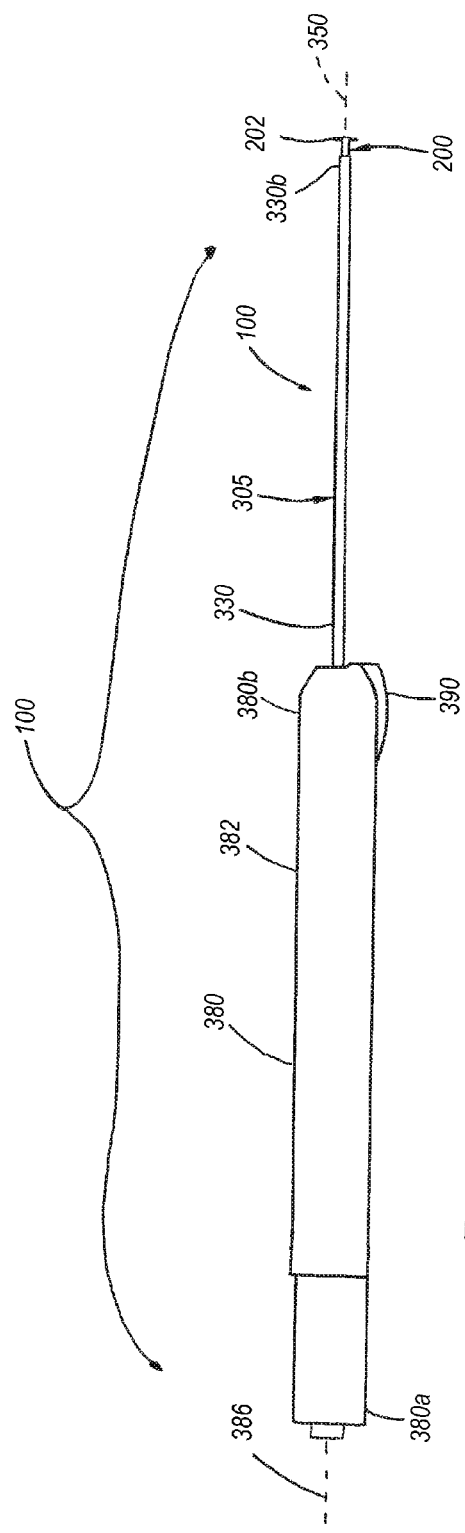
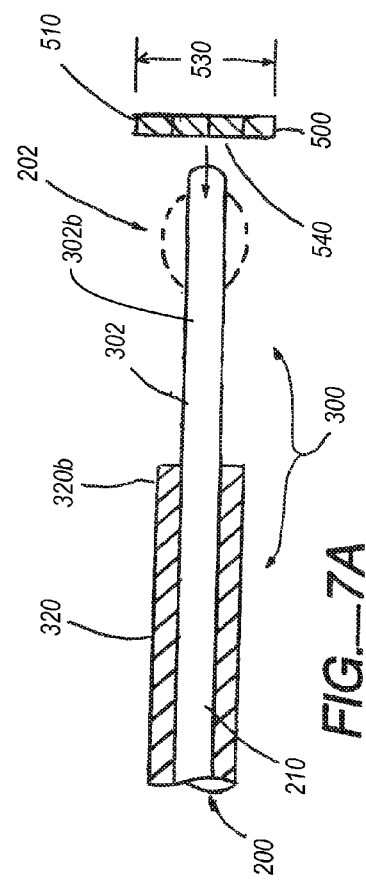
FIG.—6
FIG.—7A

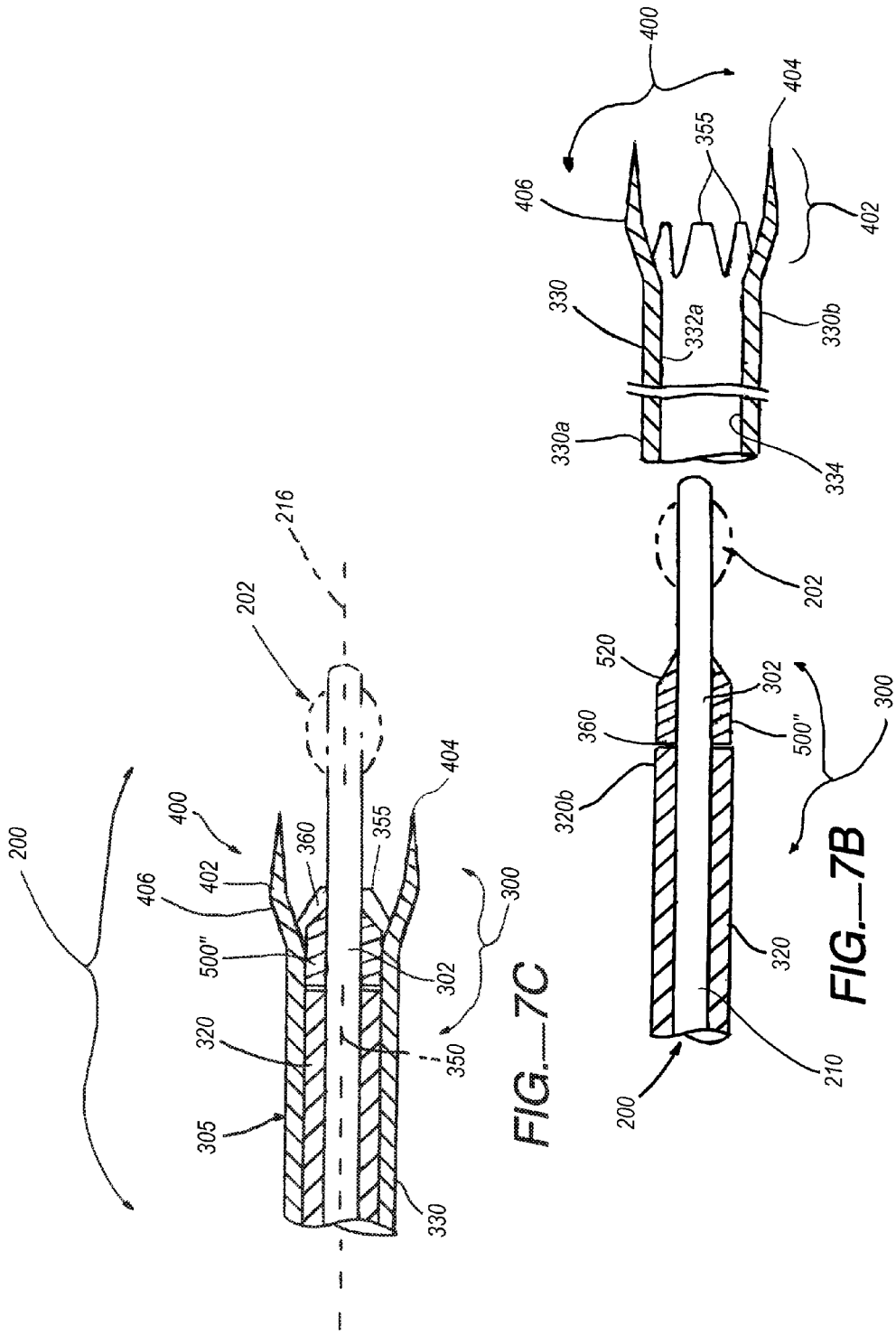

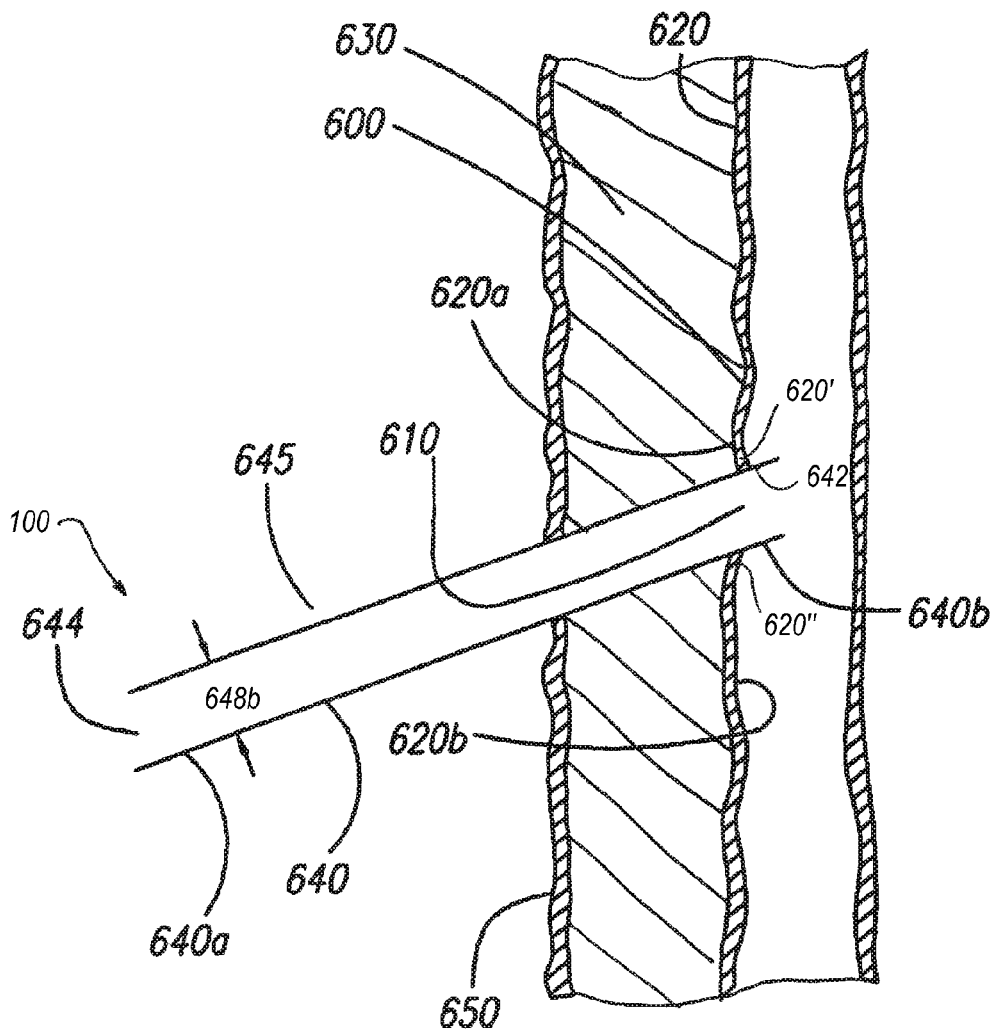
FIG._8A

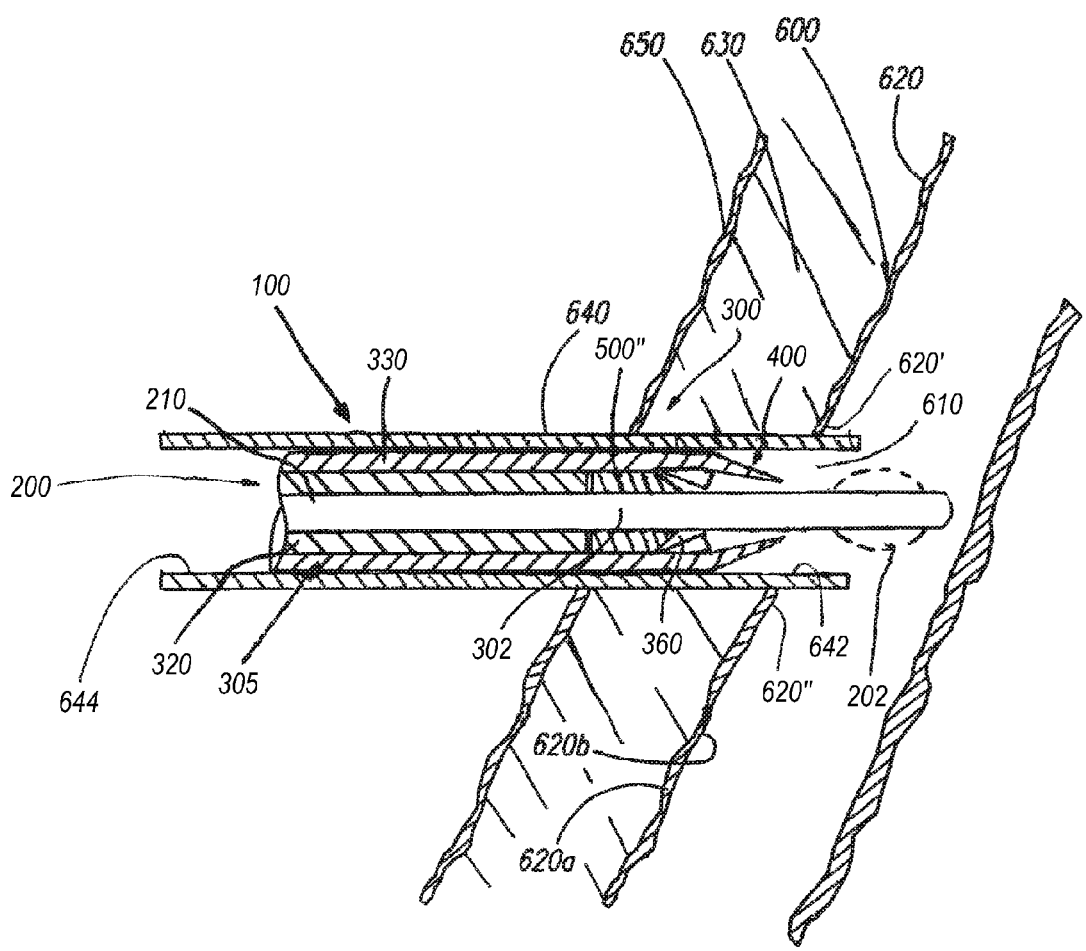
FIG._8B

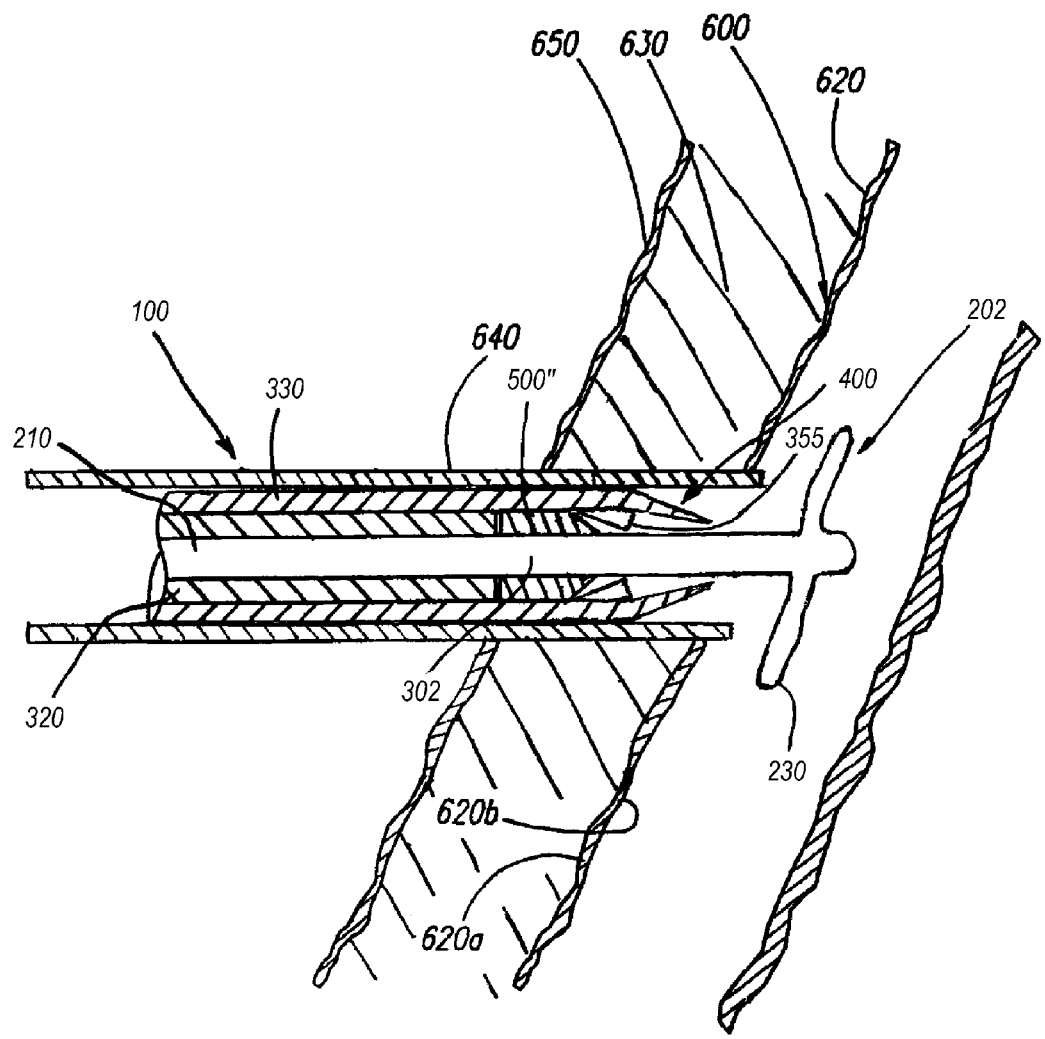
FIG._8C

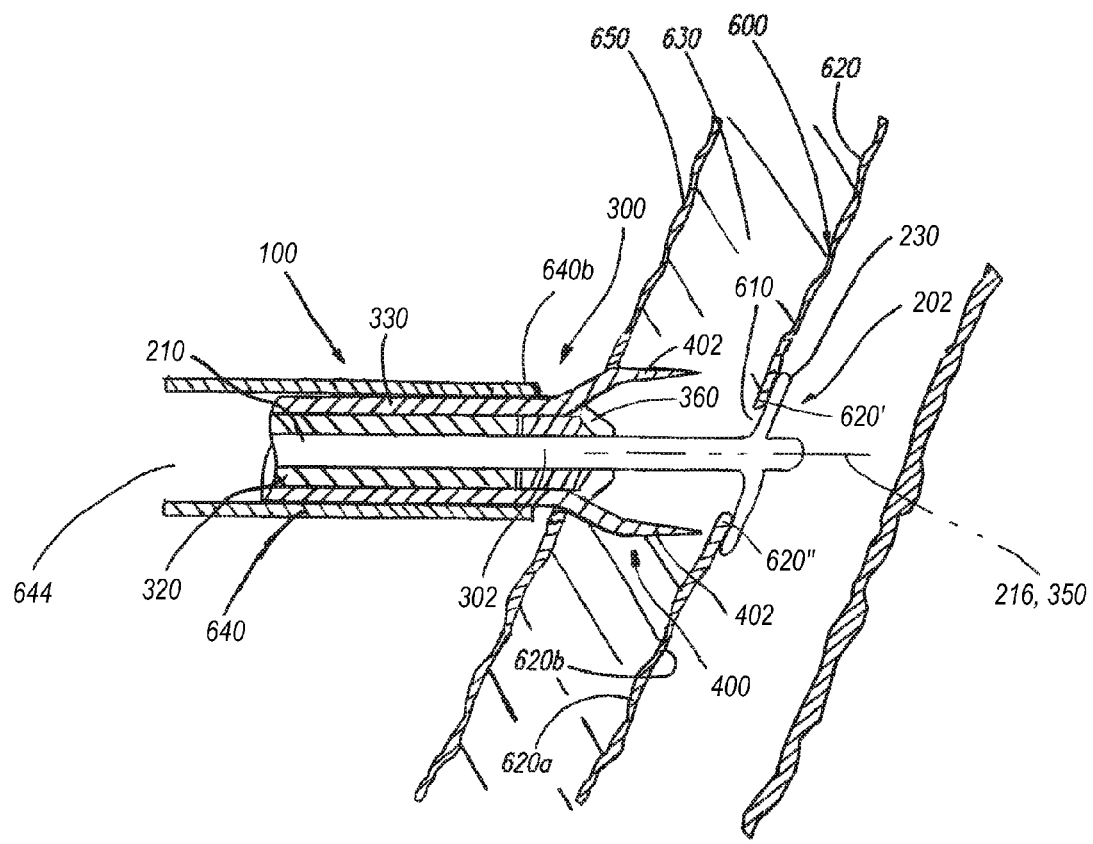
FIG._8D

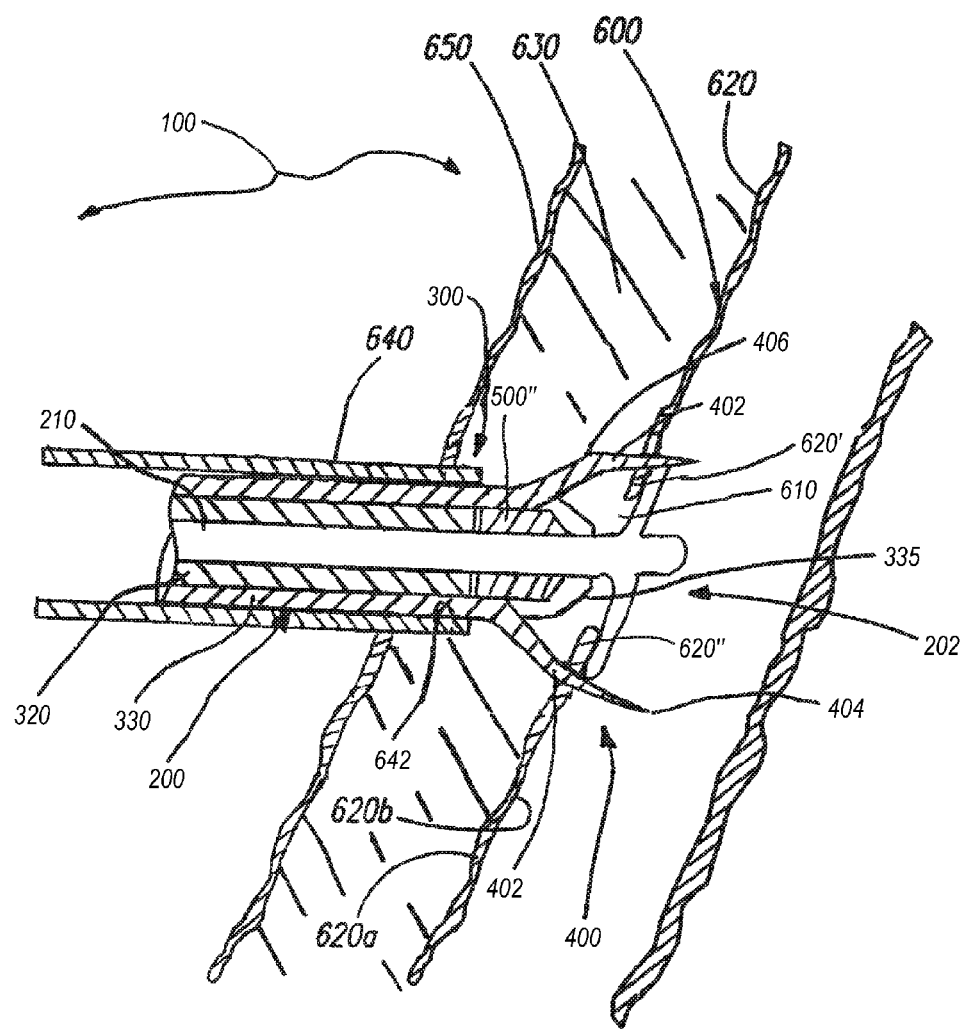
FIG._8E

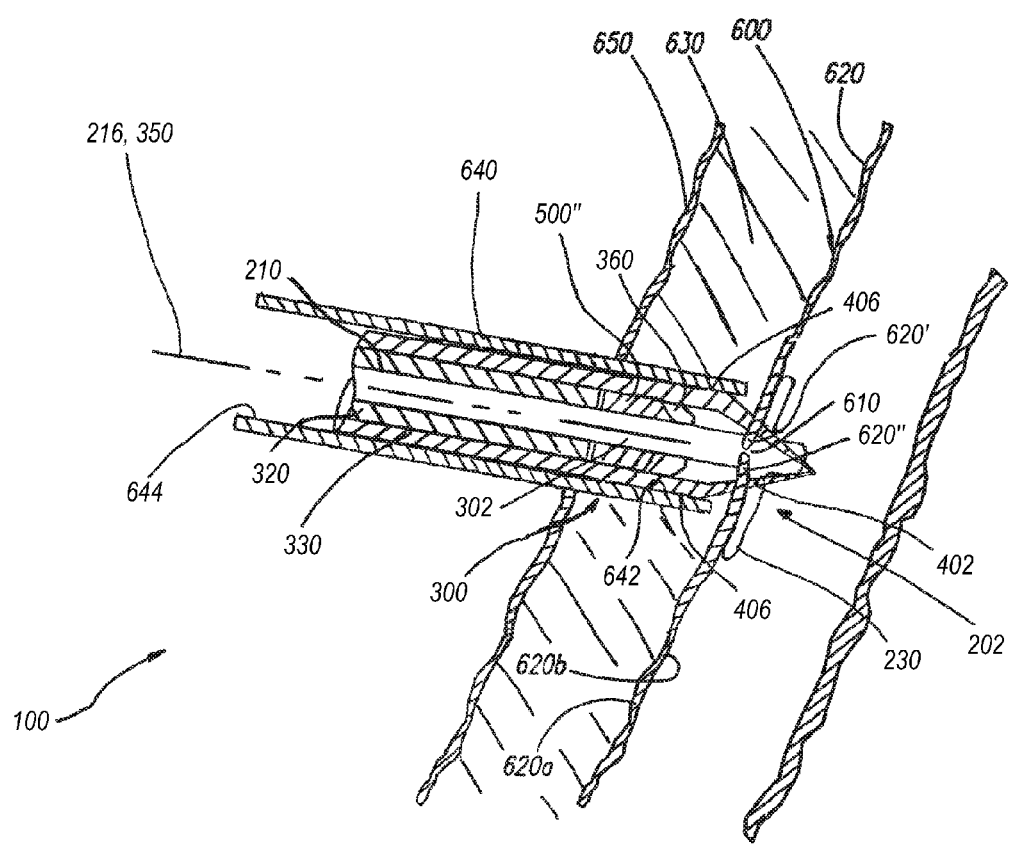
FIG._8F

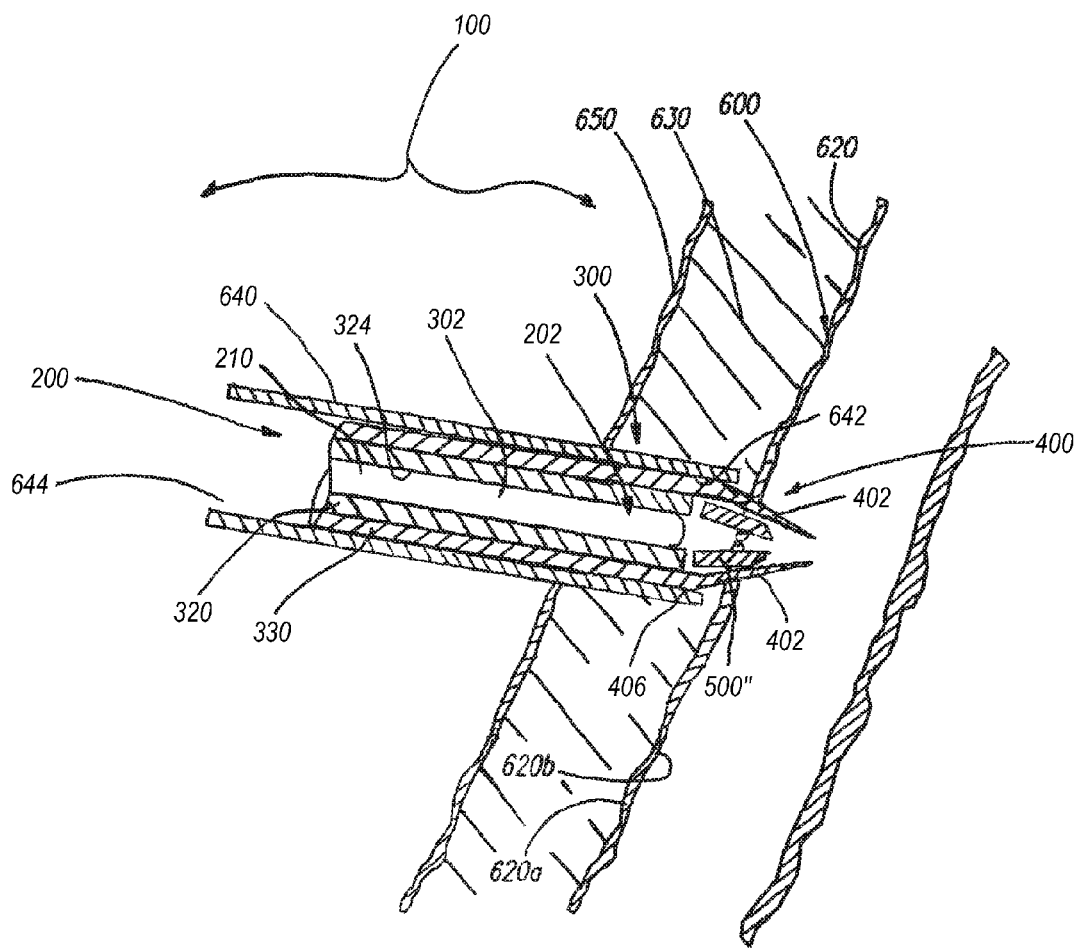
FIG._8G

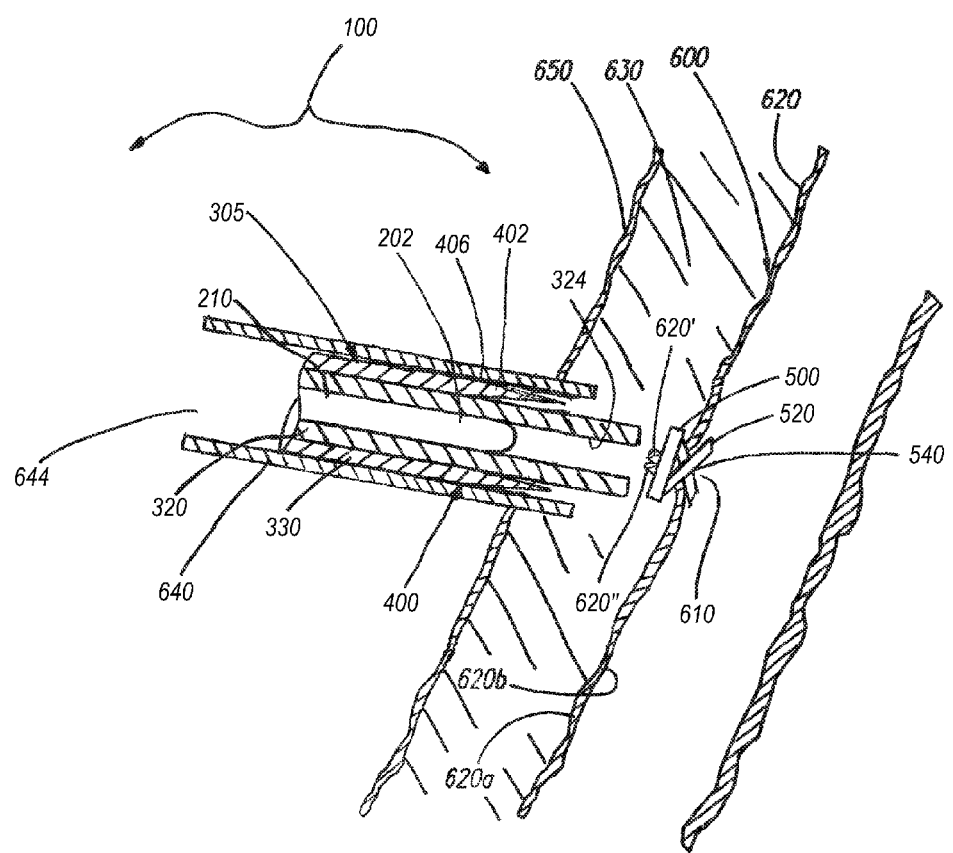
FIG._8H

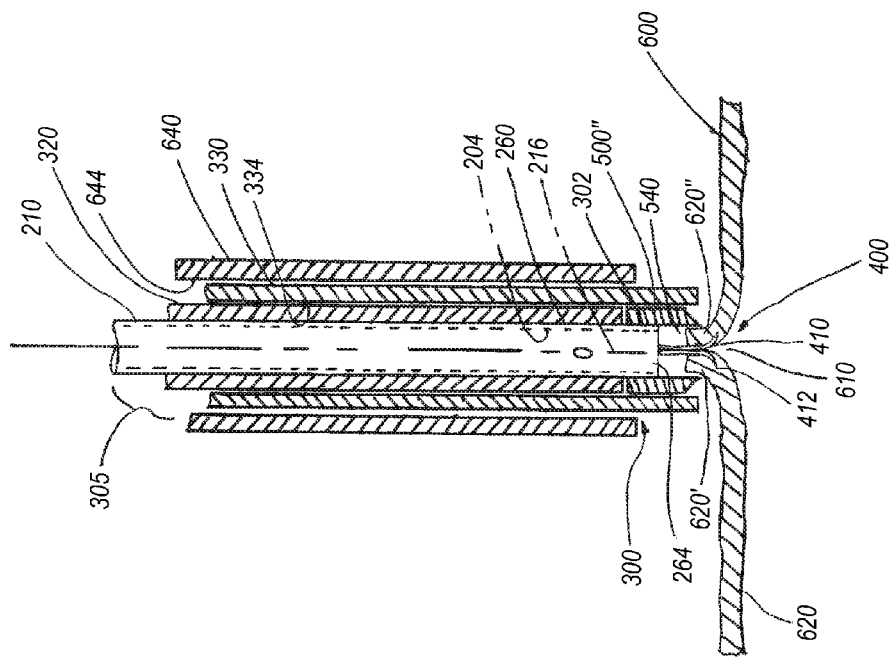
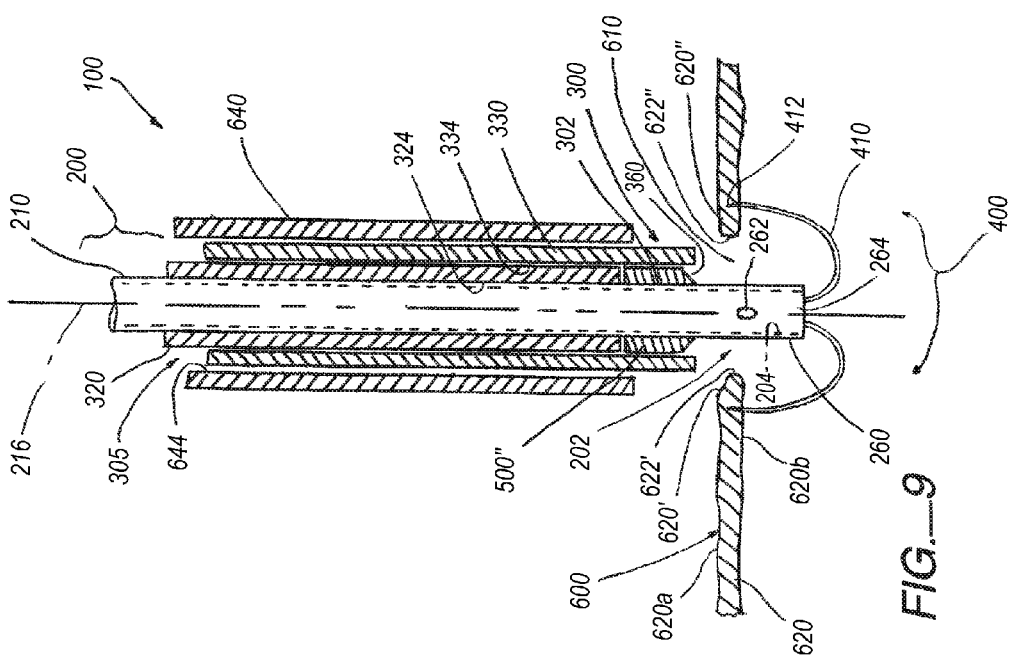

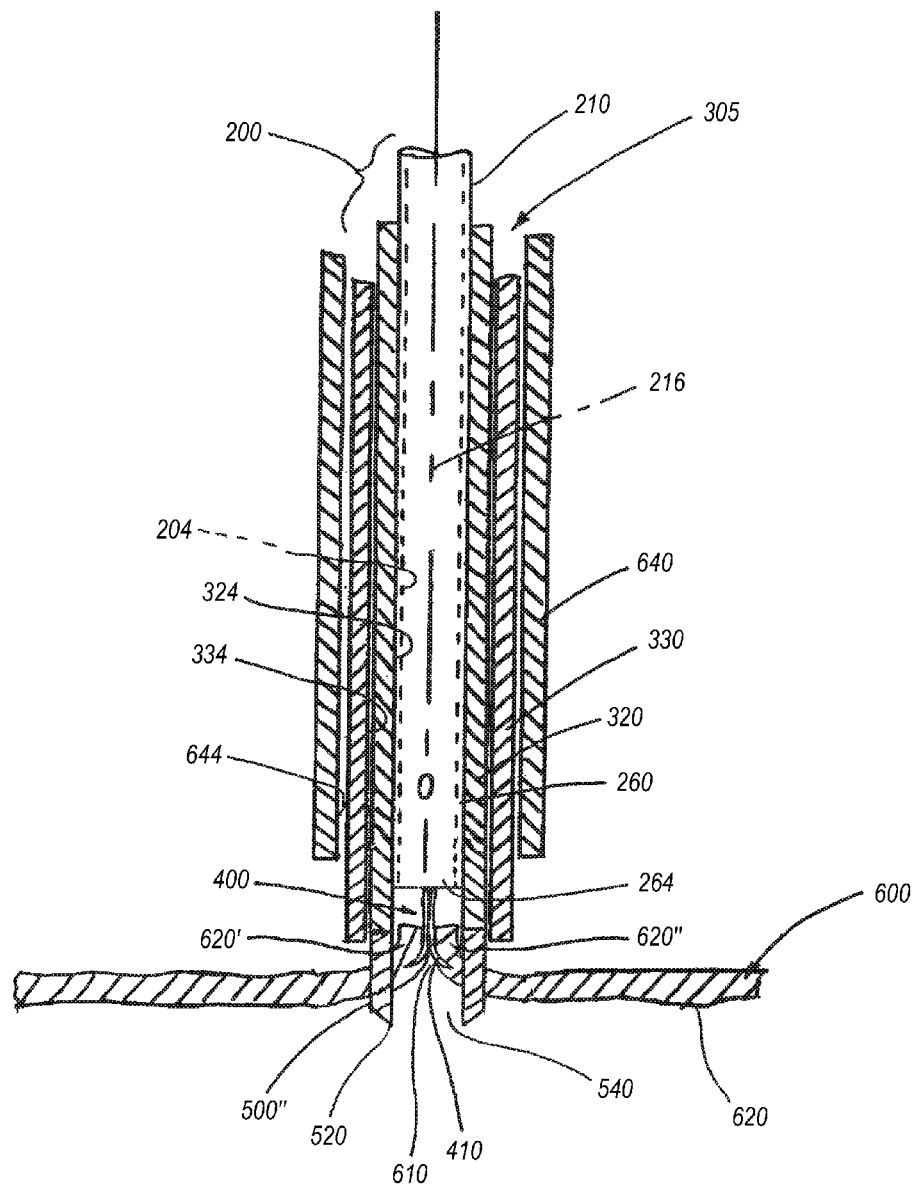
FIG._11

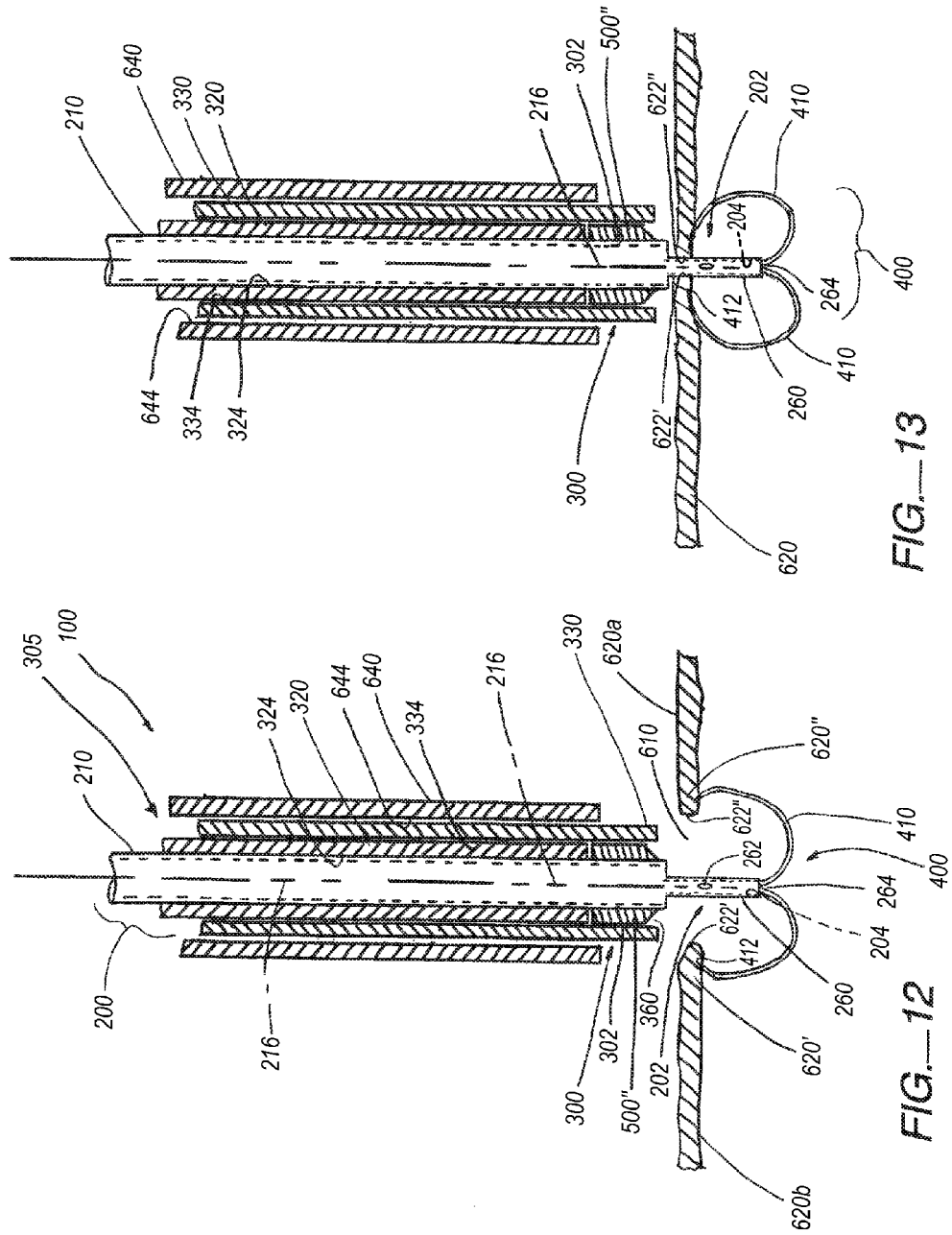

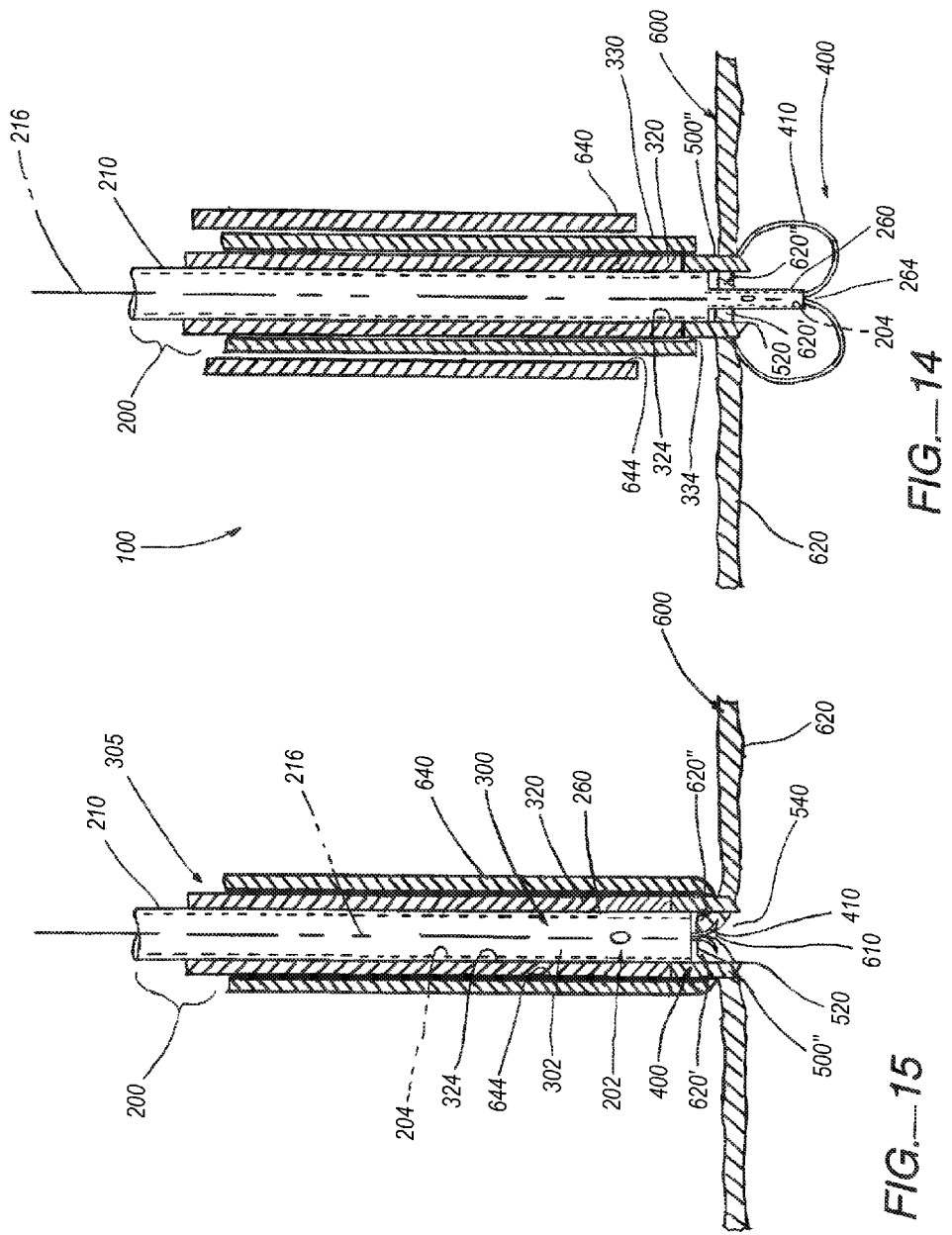

APPARATUS AND METHOD FOR DELIVERING A CLOSURE ELEMENT

CROSS-REFERENCE TO RELATED APPLICATIONS

This application claims priority to and the benefit of U.S. Provisional Patent Application No. 60/843,325, filed Sep. 8, 2006, entitled "APPARATUS AND METHOD FOR DELIVERING A CLOSURE ELEMENT," the disclosure of which is incorporated herein in its entirety by specific reference.

BACKGROUND OF THE INVENTION

1. The Field of the Invention

The present invention relates generally to an apparatus and method for closing and/or sealing openings in a body lumen and/or tissue. More particularly, the present invention relates to an apparatus and method for delivering a closure element for closing a puncture in a blood vessel or other body lumen formed during a diagnostic or therapeutic procedure.

2. The Relevant Technology

Catheterization and interventional procedures, such as angioplasty or stenting, are generally performed by inserting a hollow needle through a skin and tissue and into a vascular system. A guide wire may be advanced through the needle and into the blood vessel accessed by the needle. The needle then is removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of applied pressure. It is also uncomfortable for the patient, and requires that the patient remain immobilized in the operating room, catheter lab, or holding area. In addition, a risk of hematoma exists from bleeding before hemostasis occurs.

Various devices have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug-be positioned within the vessel, and therefore, may increase the risk of over-advancement of the plug itself into the vessel.

Alternatively, U.S. Pat. No. 5,674,231 issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, while these closure devices and procedures are met with varying degrees of success, there is always a need for a new and improved apparatus and technique for delivering a closure element to a vascular puncture site or other opening through tissue.

BRIEF SUMMARY OF THE INVENTION

The present invention is directed toward an apparatus and method for delivering a closure element through tissue and into an opening formed in, or adjacent to, a wall of a blood vessel or other body lumen of any size.

In one embodiment, the present invention includes an apparatus for positioning a closure element to close an opening in a body lumen. Such an apparatus includes a carrier assembly and a distal tissue engaging device. The carrier assembly is configured to support a closure element in a substantially tubular configuration in a first diameter. The closure element is configured to substantially uniformly deform from a substantially tubular configuration to a natural, substantially planar configuration. The distal tissue engaging device is selectably axially displaceable relative to at least a portion of the carrier assembly. As such, the distal tissue engaging device moves between a tissue engaging condition and a tissue closing condition. The tissue engaging condition engages opposing portions of an arterial wall defining said body lumen adjacent to the opening. The tissue closing condition urges the engaged opposing portions of the arterial wall substantially together such that the closure element may be deployed from the delivery assembly to engage the opposed portions of the arterial wall and to return to the natural, substantially planar configuration.

In one embodiment, the distal tissue engaging device includes two or more opposed engaging tongs having respective end tips configured to open radially in directions extending beyond the first diameter to initially engage the opposing portions of the arterial wall, in the engaging condition.

In one embodiment, the carrier assembly further includes a cover member protecting at least the closure element which is contained therein.

In one embodiment, the distal tissue engaging device is integral with a distal end of the cover member.

In one embodiment, the carrier assembly is formed and dimensioned for sliding axial, reciprocating, receipt in a lumen of an introducer sheath extending through said tissue and terminating proximate the opening. The tissue engaging device is configured to cooperate with the introducer sheath to enable movement between the engaging condition and the closing condition.

In one embodiment, the present invention includes an apparatus for delivering and deploying a substantially resilient closure element through tissue to an opening in a body lumen perimeterically defined by opposing arterial walls. The closure element is configured to substantially uniformly deform from a natural, substantially resilient planar configuration to a substantially tubular configuration having a substantially natural transverse cross-sectional dimension. The apparatus includes a delivery assembly positionable through the tissue toward the opening in the body lumen. Also, the delivery assembly has a distal tissue engaging device and a carrier assembly configured to support the closure element in the substantially tubular configuration in a first diameter. The distal tissue engaging device is selectably axially displaceable relative to at least a portion of the carrier assembly between a tissue engaging condition and a tissue closing condition. The tissue engaging condition engages the opposing arterial walls of the body lumen adjacent to the opening. The tissue closing condition urges the engaged opposing arterial walls substantially transversely together such that the closure element may be deployed from the delivery assembly, while substantially maintained in the first diameter, into the opposing arterial walls. The closure element is oriented to engage the engaged opposing arterial walls when deployed and to return to the natural, substantially planar configuration and the natural, transverse cross-sectional dimension such that the engaged opposing arterial walls are drawn substantially closed.

In one embodiment, the apparatus includes a locator configured to position the carrier assembly and distal tissue engaging device adjacent to the opening in the body lumen. Also, the locator has a distal locator portion selectably controllable between an unexpanded state and an expanded state for engaging the opposing portions of the arterial wall of the body lumen.

In one embodiment, the apparatus includes a distal tissue locator portion contained on the delivery assembly. The distal tissue locator portion is configured to facilitate detection of the body lumen and includes one or more expansion elements configured to expand substantially transversely with respect to a longitudinal axis of the distal locator portion.

In one embodiment, the distal locator portion is selectably controllable between an unexpanded state and an expanded state for engaging said opposing arterial walls of said body lumen.

In one embodiment, while in the unexpanded state, the distal locator portion has a transverse cross-sectional dimension less than that of the opening. Also, while in the expanded state, the distal locator portion has a transverse cross-sectional dimension greater than or substantially equal to that of said opening.

In one embodiment, the present invention includes an apparatus for positioning a closure element to close an opening in a body lumen. Such an apparatus includes a carrier assembly and a distal tissue engaging device. The carrier assembly has a tubular body configured to receive a closure element in a substantially tubular configuration in a first diameter prior to deployment. Also, the tubular body has a distal port. The distal tissue engaging device is disposed within the tubular body and is selectably axially displaceable from the distal port. A portion of the distal tissue engaging device is biased to selectively radially extend outwardly from a longitudinal axis of the tubular body to intravascularly engage opposing arterial walls of the body lumen. A portion of the distal tissue engaging device urges the engaged opposing portions of the arterial wall substantially together as the distal tissue engaging device moves proximally. The closure element is then deployed to engage the opposed portions of the arterial wall.

In one embodiment, the carrier assembly includes a cover member defining a lumen configured for slidable receipt of the closure element therein.

In one embodiment, the carrier assembly includes a pusher member that slides for distally deploying the closure element.

In one embodiment, the pusher member and the tubular body are disposed as a nested, telescoping tube set with a common longitudinal axis.

In one embodiment, the tubular body includes a tissue locator portion. The tissue locator portion includes a bleed back shaft having a bleed back port distally disposed on a distal end of the tubular body.

In one embodiment, the present invention includes a closure system for closing an opening formed in a body lumen perimeterically defined by opposing arterial walls. Such a closure system includes a closure element, a delivery assembly, and a pusher member. The closure element is adapted to deform from a natural, substantially resilient planar configuration to a substantially tubular configuration that has a substantially natural transverse cross-sectional dimension. The delivery assembly is capable of being positioned through the tissue and into the opening in the body lumen.

Additionally, the delivery assembly has an elongated body, a carrier assembly and a distal tissue engaging device. The carrier assembly includes a carrier seat configured to carry and peripherally support the closure element in the substantially tubular configuration in a first diameter. The distal tissue engaging device is selectably, axially displaceable relative to the carrier seat between an engaging condition and a closing condition. The engaging condition engages the opposing arterial walls of the body lumen adjacent to the opening. The closing condition urges the engaged opposing arterial walls substantially transversely together such that the closure element may be deployed from the carrier assembly, while substantially maintained in the first diameter, into the opposing arterial walls.

The pusher member is slidably disposed about the elongated body for relative axial sliding displacement therebetween. The pusher member has a contact portion disposed proximally adjacent to the closure element in order to selectively distally deploy the closure element from the carrier assembly. The closure element is deployed in the substantially tubular configuration so as to engage the opposing arterial walls and to return to the natural, substantially planar configuration and the natural, transverse cross-sectional dimension such that the engaged opposing arterial walls are drawn substantially closed.

In one embodiment, the delivery assembly includes a tubular body supporting the carrier seat. Also, the tubular body defines a central receiving lumen extending longitudinally therethrough that is configured for sliding support of the tissue engaging device for axial movement between the engaging condition and the closing condition.

In one embodiment, the pusher member comprises one or more distally extending longitudinal extensions.

In one embodiment, the closure system includes a locator slidably receivable within the pusher member and the delivery assembly.

In one embodiment, the present invention includes a method for closing an opening defined by edges of arterial walls of a body lumen. Such a method includes the following: positioning a distal end region of a carrier assembly through tissue adjacent to an opening so that a distal tissue engaging device engages opposing portions of arterial walls, the distal end region of the carrier assembly includes a carrier seat configured to seat said closure element thereon in a substantially tubular configuration, having a first diameter; urging the engaged arterial walls radially inwardly and toward one another such that at least opposed edges of the arterial walls drawn with the first diameter of the closure element; and distally deploying the closure element from the carrier assembly without further substantial radial expansion for the closure element, in the substantially tubular configuration, such that the closure element engages the arterial walls, and returns to the natural, planar configuration and the natural cross-section wherein the tissue is drawn substantially closed.

In one embodiment, the engagement of the arterial walls is performed by extravascularly engaging the arterial walls with the tissue engaging device.

In one embodiment, the engagement of the arterial walls is performed by intravascularly engaging the arterial walls with the tissue engaging device.

In one embodiment, the method includes placing a distal end region of a locator portion through tissue into the opening.

In one embodiment, the method includes engaging the arterial walls adjacent to the opening.

In one embodiment, the method includes orientating the carrier assembly proximal to the locator portion.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3A illustrates a top view of one embodiment of a closure element in a natural, planar configuration and with a natural cross-section for use with the apparatus of FIG. 1, prior to curing.

FIG. 3B illustrates a side view of the closure element of FIG. 3A.

FIG. 3C illustrates a top view of the closure element of FIGS. 3A-3B after a natural cross-section of the closure element has been reduced, via a curing process.

FIG. 3D illustrates a side view of the closure element of FIG. 3C.

FIG. 3E illustrates a side view of the closure element of FIGS. 3C-3D as the closure element transitions from the natural, planar configuration to a tubular configuration.

FIG. 3F illustrates a top view of the closure element of FIGS. 3C-3D upon completing the transition from the natural, planar configuration to a substantially tubular configuration, albeit a natural tubular configuration.

FIG. 3G illustrates a side view of the closure element of FIG. 3F.

FIG. 4A illustrates one embodiment of a distal locator portion and a carrier seat of a carrier assembly of FIG. 2, both of which are illustrated in an unexpanded state.

FIG. 4B illustrates the distal locator portion and a carrier seat of FIG. 4A, both of which are illustrated in an expanded state.

FIG. 4C illustrates one embodiment of a proximal end region of the delivery assembly of FIG. 2.

FIG. 5A illustrates one embodiment of a carrier assembly for the apparatus of FIG. 1.

FIG. 5B illustrates one embodiment of a pusher member for the carrier assembly of FIG. 5A.

FIG. 5C illustrates one embodiment of a cover member for the carrier assembly of FIG. 5A.

FIG. 6 illustrates a tube set and the delivery assembly of the apparatus of FIG. 1 mounted to a handle portion for operative manipulation thereof.

FIG. 7A illustrates the closure element of FIGS. 3A-3G prior to being disposed upon the carrier assembly of FIG. 5A.

FIG. 7B illustrates the closure element of FIGS. 3A-3G upon being disposed upon the carrier assembly of FIG. 5A, and further as the cover member of FIG. 5C receives the carrier assembly.

FIG. 7C illustrates the closure element of FIGS. 3A-3G being retained substantially within the carrier assembly of FIG. 5A when the carrier assembly is disposed substantially within the cover member of FIG. 5C.

FIG. 8A illustrates a sheath that is positioned through tissue and into an opening formed in a wall of a blood vessel, in one embodiment of the present invention.

FIG. 8B illustrates the locator portion and the carrier assembly of the delivery assembly of the apparatus being advanced distally into the blood vessel.

FIG. 8C illustrates a distal end region of the locator portion of FIG. 8B extending into the blood vessel and being transitioned into an expanded state.

FIG. 8D illustrates the distal end region of the locator portion of FIG. 8C being retracted proximally to engage an inner surface of the blood vessel wall, and the retraction of the sheath to expose the tissue engaging device, in a tissue engaging condition.

FIG. 8E illustrates engagement of the tissue engaging device of the apparatus of FIG. 8D with the blood vessel wall.

FIG. 8F illustrates movement of the tissue engaging device from the tissue engaging condition to a closing condition.

FIG. 8G illustrates the closure element being deployed and engaging tissue adjacent to the opening in the blood vessel wall.

FIG. 8H illustrates the closure element of FIG. 8G transitioning from the substantially tubular configuration to the natural, planar configuration while engaging the engaged tissue.

FIG. 9 is a side elevation view, in cross-section, of another embodiment of the clip applier apparatus having a tissue engaging device deployed from a central lumen of the tubular body, in a tissue engaging condition.

FIG. 10 is a side elevation view, in cross-section, of the clip applier apparatus of FIG. 9, illustrating the tissue engaging device in a closing condition.

FIG. 11 is a side elevation view, in cross-section, of the clip applier apparatus of FIG. 9, illustrating deployment of the closure element.

FIG. 12 is a side elevation view, in cross-section, of yet another embodiment of the clip applier apparatus also having a tissue engaging device deployed from a central lumen of the a tubular body, in a tissue engaging condition.

FIG. 13 is a side elevation view, in cross-section, of the clip applier apparatus of FIG. 12, illustrating the tissue engaging device in a closing condition.

FIG. 14 is a side elevation view, in cross-section, of the clip applier apparatus of FIG. 12, illustrating deployment of the closure element.

FIG. 15 is a side elevation view, in cross-section, of another embodiment of the clip applier apparatus also having a tissue engaging device deployed from a central lumen of a tubular body, in a tissue closing condition.

DETAILED DESCRIPTION

Figure 1:
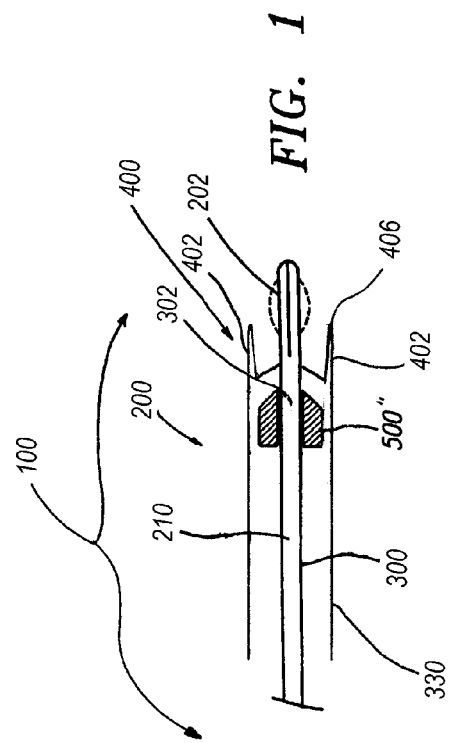
FIG. 1 provides a general illustration of an apparatus for closing openings formed in blood vessel walls constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

The apparatus is configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus preferably is configured to substantially uniformly expand the closure element beyond a natural cross-section of the closure element such that the closure element, when deployed, is configured to engage significant amount of the blood vessel wall and/or tissue. Engaging the blood vessel wall and/or tissue, the closure element is further configured to return to the natural cross-section. Thereby, the engaged blood vessel wall and/or tissue are drawn substantially closed and/or sealed, such that, for example, hemostasis within the opening is enhanced.

In one specific embodiment, an apparatus is provided for delivering and deploying a substantially resilient closure element through tissue to an opening in a body lumen perimeterically defined by opposing arterial walls. The closure element is configured to substantially uniformly deform from a natural, substantially resilient planar configuration to a substantially tubular configuration, having a substantially natural transverse cross-sectional dimension. The apparatus include a delivery assembly positionable through the tissue and into the opening in the body lumen, and having a distal tissue engaging device and a carrier assembly. The carrier assembly is configured to carry and support the closure element in the substantially tubular configuration in a first diameter. The distal tissue engaging device is selectably axially displaceable relative to at least a portion of the carrier assembly between a tissue engaging condition and a tissue closing condition. In the tissue engaging condition, the opposing arterial walls of the body lumen are engaged adjacent to the opening. In contrast, in the tissue closing condition, the engaged opposing arterial walls are urged substantially transversely together such that the closure element may be deployed from the delivery assembly, while substantially maintained in the first diameter, into the opposing arterial walls. The closure element is oriented to engage the engaged opposing arterial walls when deployed and to return to the natural, substantially planar configuration and the natural, transverse cross-sectional dimension such that the engaged opposing arterial walls are drawn substantially closed.

The distal tissue engaging device includes two or more opposed engaging tongs having respective end tips configured to open radially in directions extending beyond the first diameter of the carrier assembly to initially engage the opposing arterial walls, in the engaging condition. These engaging tongs are configured to close radially inward such that the engaged opposing arterial walls are disposed within the first diameter of the closure element, in the substantially tubular configuration, in the closing condition.

In another specific embodiment, the carrier assembly includes a cover member protecting the delivery assembly such that at least the closure element is contained therein. The cover member defines a lumen configured for slidable receipt of the closure element therein. The distal tissue engaging device is integral with a distal end of the cover member to enable movement of the two or more opposing tongs between the engaging condition and the closing condition.

Still another specific arrangement provides a delivery assembly that is formed and dimensioned for sliding axial, reciprocating, receipt in a lumen of an introducer sheath extending through the tissue and terminating proximate the opening. The tissue engaging device is configured to cooperate with the introducer sheath to enable movement between the engaging condition and the closing condition. Further, the two or more tongs are formed and dimensioned for sliding contact with the sheath lumen to effect movement between the engaging condition and the closing condition.

In yet another specific embodiment, the carrier assembly includes a carrier seat configured to seat the closure element, in the substantially tubular configuration, on the delivery assembly prior to deployment. The delivery assembly includes a tubular body supporting the carrier seat, and defines a central receiving lumen extending longitudinally therethrough that is configured for sliding support of the tissue engaging device for axial movement between the engaging condition and the closing condition. Each of the two or more tongs are bowed and biased radially outward, relative one another, from a longitudinal axis of the tubular body such that an end tip of each respective tong is urged outward and toward gripping intravascular engagement with an undersurface of the opposing arterial walls, in the engaging condition, when the tissue engaging device extends distally from the central lumen of the tubular body.

In another aspect of the present invention, a closure system is provided for closing an opening formed in a body lumen perimeterically defined by opposing arterial walls. The system includes a closure element adapted to deform from a natural, substantially resilient planar configuration to a substantially tubular configuration, having a substantially natural transverse cross-sectional dimension. A delivery assembly is positionable through the tissue and into the opening in the body lumen. The delivery assembly includes an elongated body, a carrier assembly and a distal tissue engaging device. The carrier assembly includes a carrier seat configured to carry and peripherally support the closure element in the substantially tubular configuration, in a first diameter. The distal tissue engaging device is selectably axially displaceable relative to the carrier seat between the engaging condition and the closing condition, while substantially maintaining the engaged walls within the first diameter. A pusher member is slidably disposed about the elongated body for relative axial sliding displacement therebetween. The pusher member includes a contact portion disposed proximally adjacent the closure element. The pusher member is applied to selectively distally deploy the closure element from the carrier assembly, in the substantially tubular configuration, to engage the opposing arterial walls and to return to the natural, substantially planar configuration and the natural, transverse cross-sectional dimension such that the engaged opposing arterial walls are drawn substantially closed.

In yet another aspect of the present invention, a method for closing an opening perimetrically defined by edges of the arterial walls of a body lumen is provided including placing a distal end region of a locator portion of a through tissue into the opening; and engaging the arterial walls adjacent to the opening. The method further includes positioning a distal end region of a carrier assembly through the tissue adjacent to the opening. The carrier assembly is oriented proximal to the locator portion, and the distal end region of the carrier assembly includes a carrier seat configured to seat the closure element thereon in a substantially tubular configuration, having a first diameter. The method includes urging the engaged arterial walls radially inward and toward one another such that at least opposed edges of the arterial walls drawn with the first diameter of the closure element. The closure element is distally deployed from the carrier assembly without further substantial radial expansion for the closure element, in the substantially tubular configuration, such that the closure element engages the arterial walls, and returns to the natural, planar configuration and the natural cross-section wherein the tissue is drawn substantially closed.

In one specific embodiment, the engaging of the arterial walls is performed by extravascularly engaging the arterial walls with a tissue engaging device. In contrast, the engaging of the arterial walls is performed by intravascularly engaging the arterial walls with a tissue engaging device.

Referring now generally to FIGS. 1-4 and 8A-8H, a clip or closure applier apparatus, generally designated 100, is provided for delivering and deploying a closure element 500 to an opening 610 formed in a body lumen, such as a blood vessel 600; the opening 610 of which is perimeterically defined by opposing tissue arterial walls 620', 620" (FIG. 8A). Briefly, as shown in FIGS. 3A-3G, the closure element 500 itself is configured to resiliently deform between a natural, substantially planar configuration (after a curing process (FIG. 3C)) to a substantially tubular configuration (FIGS. 3F and 3G). Further, the closure element can also be resiliently deformed and radially displaced up to an expanded substantially tubular configuration, having a greater cross-sectional dimension, from its natural substantially tubular configuration (FIGS. 8F and 8G), or can be displaced down to a reduced substantially tubular configuration, having a lesser cross-sectional dimension.

Returning to the clip applier apparatus 100, in accordance with the present invention, a delivery assembly, generally designated 200, is included that is positionable through the tissue 630 and into the opening 610. The delivery assembly 200 includes a distal tissue engaging device 400 and a carrier assembly 300, oriented just proximal to the distal tissue engaging device, that houses and supports the closure element 500". The carrier assembly 300 includes a carrier seat portion 302 configured to carry and support the closure element 500" in a slightly expanded substantially tubular configuration (FIG. 7A-7C), in a first diameter, that is slightly greater than that in a natural, substantially tubular condition.

The distal tissue engaging device 400 is selectably axially displaceable relative to the carrier assembly 300 between a tissue engaging condition (FIG. 8D) and a tissue closing condition (FIG. 8F). In the tissue engaging condition, the tissue engaging device 400 engages the opposing arterial walls 620', 620" (e.g., FIG. 8D-8E) of the body vessel 600 adjacent to the opening 610 so that the engaged walls can be pulled or urged radially inward or transversely toward one another in the closing condition (FIG. 8F-8G). Hence, in the closing condition, the engaging device 400 urges the opposing arterial walls 620', 620" at the opening 610, substantially closer together and toward one another radially. By closing the opposing arterial walls within the first diameter of the closure element 500" (mounted about the carrier seat 302 in the substantially tubular configuration), the closure element can be deployed directly there from without having to further radially expand the same to sufficiently engage the tissue.

Hence, applying a pusher member 320 (as will be described), the closure element 500", which is retained in the substantially tubular configuration, can be deployed into the opposing arterial walls (FIG. 8G). Subsequently, once the closure element engages the opposing arterial walls 620', 620" and is released from the delivery assembly, it returns to the natural, substantially planar configuration and the natural cross-section dimension such that the engaged opposing arterial walls are drawn substantially closed (FIG. 8H).

In accordance with the present invention, since the closure element 500" can be deployed from the closure applier apparatus 100 without requiring substantial further radial expansion from the substantially tubular configuration atop the carrier assembly, the overall complexity of the closure applier can be significantly reduced. In turn, the diametric footprint can be significantly reduced, as compared to previous designs, which in effect permit the use of a smaller diameter GF introducer sheath. Moreover, a closure applier apparatus is provided that fully encloses the closure element within itself during advancement to the tissue site, prior to deployment and delivery to the targeted vessel walls. Unlike many current designs, the present invention significantly reduces potential tissue snag or contact by the closure element during advancement and positioning. This enclosure approach is similar to those disclosed in co-pending U.S. patent application Ser. No. 11/455,993, filed Jun. 19, 2006, and entitled "APPARATUS AND METHOD FOR DELIVERING A CLOSURE ELEMENT"; and U.S. patent application Ser. No. 10/356,214, filed Jan. 30, 2003, entitled "CLIP APPLIER AND METHODS OF USE" (hereinafter referred to as the '214 patent application), each of which is herein incorporated by reference in their entirely. These designs prove much more desirable and provide a basis for a wide range of medical applications, such as diagnostic and/or therapeutic procedures involving blood vessels or other body lumens of any size.

As will be discussed in more detail below, the clip applier apparatus 100 can deliver a closure element 500" (shown in FIGS. 3F-G) through tissue 630 (shown in FIG. 8A) and into an opening 610 formed in and/or adjacent to and perimeterically defined perimetrically by the arterial walls 620 (e.g., the opposed arterial walls 620', 620") of a blood vessel 600 or other body lumen. The closure element (or clip) 500 preferably has a generally annular-shape body 510 (shown in FIGS. 3A-3B) defining a channel 540 and one or more barbs and/or tines 520 for receiving and engaging the blood vessel wall 620 and/or the tissue 630 around the opening 610. Although the closure element 500, when originally fabricated, has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 3A-3B. Via a heat-treating process, disclosed in U.S. Pat. No. 6,623,510 to Carley et al., incorporated herein by reference in its entirety, the natural cross-section 530 of the closure element 500 will be reduced to form a reduced closure element 500' that has a natural, planar configuration with opposing tines 520 and a reduced cross-section 530' as shown in FIGS. 3C-3D. By rotating the opposing tines 520 axially as shown in FIG. 3E, the cured closure element 500' can be further deformed to form a substantially tubular closure element 500" (shown in FIG. 3F) having a generally annular-shape body 510' with an outer diameter 530' and an inner diameter 550. In this substantially tubular configuration with the tines 520 in an axial configuration (FIG. 3G which is the configuration when loaded on the carrier assembly configuration, albeit slightly expanded), the resulting cross-section 530' when loaded is expanded as well.

Being configured to draw the opposed blood vessel arterial walls 620', 620" and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof As desired, the closure element 500 can include radiopaque markers (not shown) or can be wholly or partially formed from a radiopaque material to facilitate observation of the closure element 500 using fluoroscopy or other imaging systems. Exemplary embodiments of a closure element are disclosed in U.S. Pat. No. 6,197,042, in co-pending application Ser. Nos. 09/546,998; 09/610,238 and 10/081, 726. The disclosures of these references and any others cited therein are expressly incorporated herein by reference.

With the exception of the last specific embodiment shown in FIG. 15, the clip applier apparatus 100 is configured to receive, retain and substantially enclose the closure element 500" within the apparatus 100. In the embodiments of FIGS. 1-2 and 4-15, as will be described in greater detail below, the delivery assembly 200 includes an elongated tubular body 210 that supports a distal tissue locator portion 202 and the carrier seat 302 of the carrier assembly 300 that is disposed proximal to the locator portion. The carrier assembly 300 further includes a cylindrical cover member or garage tube 330 enclosing the pusher member 320, the tubular body 210 and the carrier seat 302 in a nested manner within its receiving lumen 334 until the closure element is prepared for deployment.

In each embodiment, if the apparatus 100 is introduced via an introducer sheath 640 (shown in FIG. 8A), for example, the closure element 500" can be disposed entirely within the garage tube 330, and delivered by way of the lumen 644 (shown in FIG. 8A) of the introducer sheath 640. Being disposed substantially within the garage tube 330 of the clip applier apparatus 100 just prior to deployment of the closure element 500", the delivery assembly 200 can deeply penetrate the tissue 630 adjacent to the opening 610 without inadvertently contacting or snaring it. The delivery assembly 200 can thus position the closure element 500" substantially adjacent to an outer surface 620a (shown in FIG. 8A) of the blood vessel wall 620 adjacent to the opening 610.

Referring to the specific embodiments of FIGS. 1-2 and 4-15, each clip applier apparatus 100 includes a central distal tissue locator portion 202 and a carrier assembly 300 supported on the end of, and integrated with, the tubular body 210 of the delivery assembly 200. Briefly, the distal locator portion 202 is configured to facilitate location of the opening 610 into the blood vessel 600, relative to the carrier assembly 300 and the tissue engaging device 400 (e.g., FIGS. 8D and 8E).

The carrier assembly 300, on the other hand, is configured to carry and support the closure element 500" in the substantially tubular configuration (FIGS. 3F and 3G), albeit in a slightly expanded configuration from its natural tubular configuration. In this manner, the resiliency of the closure element 500" itself, together with the confinement of the cover member 330, function to secure it to the carrier seat 302 of the carrier assembly 300. When deployed, the closure element 500" (in the substantially tubular configuration) is oriented with its tines directed distally to engage the blood vessel wall 620 and/or the tissue 630 around the opening 610, and to return to the natural, substantially planar configuration and the natural cross-section such that the engaged tissue is drawn substantially closed (FIG. 8H).

Once strategically oriented, the clip applier apparatus 100 can be activated to distally deploy the closure element 500". It will be appreciated that although the closure element 500" is capable of significantly greater radial expansion from its tubular configuration mounted to the carrier assembly 300 of the tubular body 210, the delivery assembly is designed to deploy the closure element 500" directly from the carrier seat 302 without requiring any further significant radial expansion.

The apparatus 100 can be provided as one or more integrated components and/or discrete components. As shown in the embodiment of FIGS. 1-2 and 4-8, for example, the apparatus 100 can include an elongated delivery assembly 200 having an integral tissue engaging device 400, central vessel locator (or obturator) portion 202 and carrier assembly 300, that carries the closure element 500" thereon, on a single subsystem. In contrast, in the embodiments of FIGS. 9-15, the tissue engaging device 400 is contained on a separate subsystem from the carrier assembly 300 and the vessel locator portion 202, all of which cooperate with one another to deploy the closure element.

In fact, in accordance with the present invention, it is the position, implementation and execution of the tissue engaging device 400 that differentiates each embodiment. In one specific embodiment, for example, the tissue engaging device 400 is disposed on the distal end to the cover member 330 (FIGS. 1-2, and 4-8), where it is selectively operated between the tissue engaging condition (FIGS. 8D, 8E) and the closing condition (FIGS. 8F, 8G). In contrast, in the embodiments of FIGS. 9-15, the tissue engaging device 400 is disposed within a central lumen 204 of the tissue locator portion 202, and is selectively operated as it is distally advanced from the lumen. It will be appreciated that these differing implementations of the tissue engaging devices will each be detailed separately below.

In each implementations, however, the tissue engaging device 400 is capable of gripping, snaring and/or piercing the tissue arterial walls 620, and urging them together and radially inward, toward one another, such that portions of the arterial walls 620', 620" are axially contained within the first diameter of the closure element 500", in the substantially tubular configuration. As mentioned, this arrangement enables the deployment of the closure element 500" directly from the carrier seat 302 of the carrier assembly 300 without requiring further radial expansion.

Referring back to FIGS. 4-8, the first specific embodiment will be described in detail. In this particular arrangement, the distal tissue locator portion 202 (obturator) is configured to extend into the opening 610 and selectably engage an inner surface 620b of the blood vessel wall 620 (FIG. 8D). Thereby, the distal locator portion 202 is configured to draw the blood vessel wall 620 taut, and maintain the proper position of the clip applier apparatus 100 as the blood vessel 600 pulsates. Briefly, in cooperation with the tissue engaging device 400 oriented at the distal end of the cover member 330, once the distal locator portion 202 is properly aligned and positioned, the tissue engaging device can be operated to engage the arterial walls, drawing them radially together as will be described below.

Figure 2:
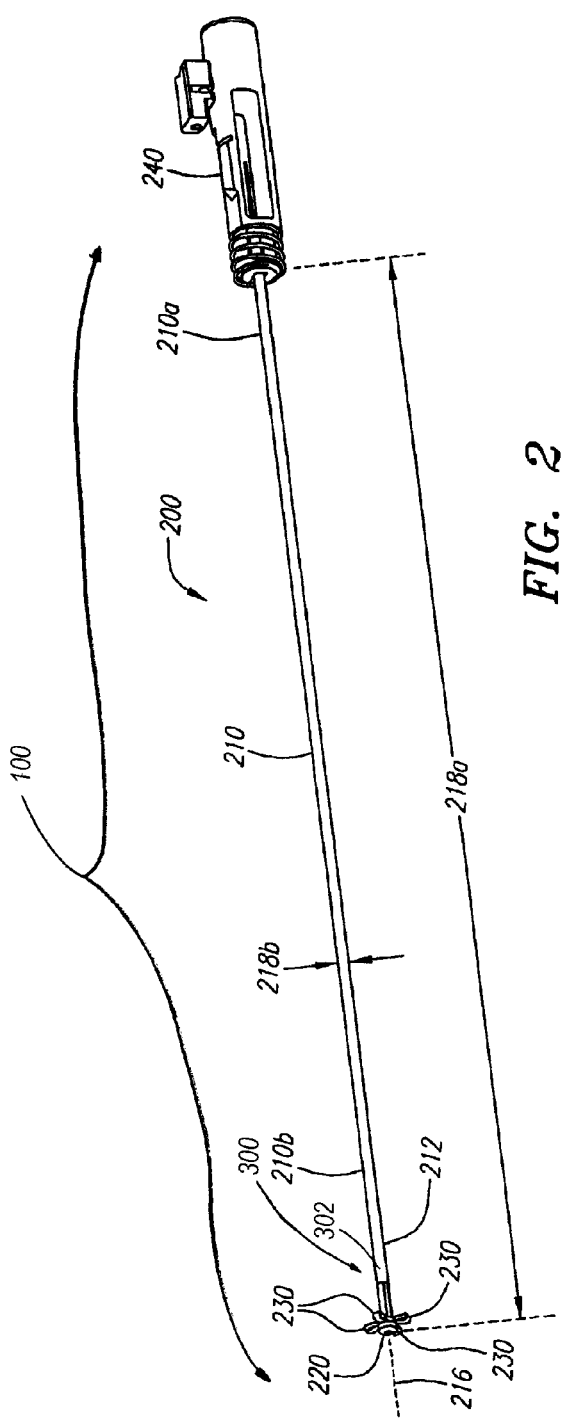
FIG. 2 illustrates one embodiment of a delivery assembly for the apparatus of FIG. 1.

First, the delivery assembly 200 of this embodiment will be detailed which includes the tubular body 210, the carrier assembly 300 and the distal locator portion 202 integrated on a single subsystem. The tubular body 210 is preferably provided by a flexible, semi-rigid or rigid, tubular structure, such as an elongate rail, with a longitudinal axis 216. As illustrated in FIGS. 2 and 4A, the tubular body 210 has a proximal end region 210a and a distal end region 210b that supports the carrier seat 302 of the carrier assembly 300 just proximal to the distal locator portion 202.

The tubular body 210 is preferably of a predetermined length 218a and a predetermined outer cross-section 218b (FIG. 2), both of which can be of any suitable dimension. The distal section of the distal locator portion 202 preferably includes a substantially rounded, soft, and/or flexible distal end or tip 220 to facilitate atraumatic advancement and/or retraction of the distal section into the blood vessel 600. As desired, a pigtail (not shown) may be provided on the distal end 220 to further aid atraumatic advancement of the delivery assembly 200.

Turning now to FIGS. 4A and 4B, it will be appreciated that the distal locator portion 202 functions in a manner similar to those disclosed in co-pending application Ser. Nos. 09/732, 835 and 10/081,723, the disclosure of which is expressly incorporated herein by reference. That is, the distal locator portion 202 is selectably controllable between an unexpanded state (FIG. 4A) and an expanded state (FIG. 4B). In the unexpanded state, the distal locator portion 202 has an unexpanded size; whereas, in the expanded state, it has an expanded size, which is greater than the unexpanded size in the unexpanded state. The distal locator portion 202 is configured to expand from the unexpanded size to the expanded size and/or to contract from the expanded size to the unexpanded size, and the expansion and contraction of the distal locator portion 202 preferably is substantially uniform about the longitudinal axis 216. For example, one or more expansion elements 230 can be provided on the distal locator portion 202 and can be configured to expand substantially transversely with respect to a longitudinal axis 216 of the locator portion 202. Preferably being substantially equally distributed about an outer periphery 212 of the distal locator portion 202, the expansion elements 230 may include radiopaque markers (not shown) or may be wholly or partially formed from a radiopaque material to facilitate observation of the expansion elements 230 and/or the distal locator portion 202 using fluoroscopy or other imaging systems.

At least one, and preferably all, of the expansion elements 230 of the distal locator portion 202 can comprise a substantially flexible member 230' with a substantially fixed end region 230a', an intermediate region 230b', and a movable end region 230c' as shown in FIGS. 4A-4B. For each substantially flexible member 230', the proximal fixed end region 230a' is fixedly coupled, relatively, with an intermediary support region 211 separating the distal locator portion 202 from the carrier assembly 300. In contrast, the movable end region 230c' is movably coupled, relatively, with the intermediary support region 211, and configured to be axially movable relative to the fixed end region 230a'. When each movable end region 230c' is axially moved toward the relevant fixed end region 230a', the intermediate regions 230b' buckle and/or expand transversely outwardly, thereby transitioning the distal locator portion 202 of the delivery assembly 200 from the unexpanded state to the expanded state. In contrast, the distal locator portion 202 transitions from the expanded state to the unexpanded state as each of the movable end regions 230c' are axially moved away from the relevant fixed end region 230a'.

Hence, the expansion elements 230 are relatively resilient, and can buckle without plastic deformation or pure elastic deformation. Further, although the expansion elements 230 are shown as comprising the flexible members 230' in FIGS. 4A-4B for purposes of illustration, it is understood that the expansion elements 230 can comprise any type of expansion elements and are not limited to the illustrated embodiments. For example, inflatable bladder type devices or the like may be employed to cause expansion of the expansion elements, such as a balloon, an expandable mesh or a slit hypotube, etc. In a preferred embodiment, the flexible members are constructed of nitinol.

Referring back to FIGS. 1 and 4-6, the delivery assembly 200 also includes the carrier assembly 300 positioned along the distal end of the tubular body 210, and oriented adjacent and proximate to the distal locator portion 202. The carrier assembly 300 is configured to receive and retain the closure element 500" in the slightly expanded, substantially tubular configuration (shown in FIG. 7B), which preferably is disposed substantially within the cover member 330 of the carrier assembly 300. The carrier assembly 300 includes a substantially cylindrical-shaped carrier seat 302 configured to seat the closure element 500" thereagainst. By parking the closure element 500" within the garage tube 330 (or cover member) during vessel advancement or positioning, not only is any tissue snaring caused by the closure element reduced, but the closure element itself is protected within the confines of the cover member.

Turning now to FIGS. 5A-5C, the carrier assembly 300 preferably includes the carrier seat 302, the pusher member 320, and the cover member (garage tube) 330. These components are preferably provided as a plurality of nested, telescoping members with a common longitudinal axis 350. As mentioned, the substantially cylindrical-shaped seat surface or the carrier seat 302 is sized and dimensioned to have transverse cross-sectional dimension slightly greater than that of the closure element 500", when the closure element is deformed to its natural substantially tubular configuration. Thus, the closure element 500 preferably is deformed from its natural, planar configuration (FIGS. 3A, 3B) to the natural, substantially tubular closure element 500" (shown in FIGS. 3F, 3G). When being placed or positioned about an outer periphery of the carrier seat 302, the closure element must further be slightly radially expanded to fit thereover. In this arrangement, the tines 520 of the substantially tubular closure element 500" are pointed substantially distally and ready for tissue engagement. Once seated, the closure element 500" will primarily be retained in place using its own resiliency toward the natural planar position from the slightly expanded, substantially tubular configuration about the seat surface.

A biocompatible glue or adhesive may further be applied to facilitate retaining the closure element 500" on the carrier seat 302 of the carrier assembly 300. Together with the internal restrictive or confining nature of the cover member 330, the glue or adhesive must be sufficient to overcome the resilient tendency of the closure element 500" (FIG. 3G) to return to its natural planar condition (FIGS. 3A and 3B). By way of example, such glues and embedded adhesives include polymer coatings, Loctite, etc. It will further be appreciated that other techniques can be applied to retain the closure element 500" to the carrier seat 302.

In accordance with the present invention, the pusher member 320 is configured to slidably receive at least a portion of the carrier seat 302, as well as the tubular body 210, with a receiving lumen 324 therein and an external surface 322b. The pusher member 320 is of a predetermined length 328a and a predetermined cross-section 328b, both of which can be of any suitable dimension. The predetermined length 328a of the pusher member 320 can be greater than or substantially equal to the collective predetermined length 218a and diameter 218b of the tubular body 210 and the carrier assembly 300. The predetermined length 328a of the pusher member 320, however, is preferably less than the collective predetermined length 218a of the tubular body 210 and the carrier seat 302, such that a distal end region 320b of the pusher member 320 is axially offset proximally from the distal end region 302b of the carrier seat 302. This axial offset, together with the cover member 330, defines an annular space 360 designated for receipt of the substantially tubular closure element 500" about the carrier seat 302.

Being formed from a substantially rigid, semi-rigid, or flexible material, the pusher member 320 preferably is substantially tubular and defines receiving lumen 324 that extends substantially between the proximal end region 320a and the distal end region 320b. This lumen 324 is configured to slidably receive at least a portion of the tubular body 210 and the carrier seat 302 therethrough. The cross-section 328b of the pusher member 320 preferably is substantially uniform, and the distal end region 320b of the pusher member 320 can comprise one or more longitudinal extensions 325, which extend distally from the pusher member 320 and along the periphery of the carrier seat 302, as shown in FIG. 5B. The longitudinal extensions 325 preferably are biased such that the longitudinal extensions 325 extend generally in parallel with common longitudinal axis 350. The longitudinal extensions 325 are sufficiently flexible to expand radially, and yet sufficiently rigid to inhibit buckling.

As best shown in FIGS. 5A and 5C, the cover member 330 is configured to retain the substantially tubular closure element 500" and the carrier assembly 300 substantially within a lumen 334 thereof prior to deployment. Being coupled with, and slidable relative to, the carrier seat 302 and the pusher member 320, the cover member 330 has a proximal end region 330a and a distal end region 330b and includes a predetermined length 338a and a predetermined cross-section 338b. Preferably being formed as a substantially rigid, semi-rigid, or flexible tubular member formed from a polymer, the cover member 330 has an outer periphery 332b and an inner periphery 332a that defines lumen 334. The lumen 334 extends substantially between the proximal and distal end regions 330a, 330b of the cover member 330 and can be configured to slidably receive at least a portion of the pusher member 320. When the cover member 330 is properly positioned over the pusher member 320 and the carrier seat 302, the distal end region 330b is configured to extend over the space 360, thereby defining an annular cavity for receiving and retaining the closure element 500" in the substantially tubular configuration.

In one preferred embodiment, as best illustrated in FIGS. 5A, 5C, 7B and 7C, one or more longitudinal extensions 335 extend distally from the garage tube or cover member 330. Although the longitudinal extensions 335 can extend generally in parallel with common longitudinal axis 350, the longitudinal extensions 335 preferably are biased such that the plurality of longitudinal extensions 335 extend substantially radially inwardly as illustrated in FIGS. 5A and 5C. Thereby, the longitudinal extensions 335 can at least partially close the annular space 360 slotted for seating of the closure element 500".

The cross-section 338b of the cover member 330 preferably is substantially uniform. In the embodiment of FIGS. 1, 2 and 4-8, the distal end region 330b of the cover member 330 is integrated with the tissue engaging device 400, as will soon be detailed. To permit the substantially tubular closure element 500" to be deployed from the annular space 360, the cover member 330 can be slidably retracted, relative the carrier seat 302 to expose the mounted closure element 500".

If the carrier assembly 300 is assembled as a plurality of nested, telescoping members as shown in FIG. 5A, the tubular body 210 of the delivery assembly is at least partially disposed within, and slidable relative to, the lumen 324 of the pusher member 320. The pusher member 320, in turn, is at least partially disposed within, and slidable relative to, the lumen 334 of the cover member 330. Hence, the longitudinal axis 216 of the locator portion 202, the carrier assembly 300 and the tubular body 210 (i.e., of the delivery assembly 200) are preferably substantially in axial alignment with the common longitudinal axis 350 of the pusher member 320 and the cover member 330.

In accordance with this embodiment of the present invention, the tissue engaging device 400 is disposed and oriented on the distal end of the cover member 330 for operation between the tissue engaging condition (FIGS. 8D, 8E) and the tissue closing condition (FIGS. 8F, 8G). As previously indicated, in the tissue engaging condition, the tissue engaging device 400 engages the opposing arterial walls 620', 620" (e.g., FIG. 8E) of the vessel 600 adjacent to the opening 610 so that they can be pulled or urged radially inward or transversely toward one another in the closing condition (FIG. 8F). In the closing condition, hence, the engaging device 400 urges the opposing arterial walls 620', 620" at the vessel opening 610, substantially radially together about axis 216 and toward one another. By closing the opposing arterial walls within the first diameter of the closure element 500", the closure element can be deployed directly from the carrier seat 302 of the carrier assembly 300 without having to further radially expand to sufficiently engage the tissue.

As best illustrated in FIG. 7B, the engaging device 400 includes at least two opposing tongs 402, each of which extends distally from the distal end of the cover member and terminates at a tissue engaging tip 404. The tips 404 may be conventionally pointed shaped that facilitate penetration and/or snaring of tissue during operation. These tongs, preferably integral with the cover member or garage tube 330, are sufficiently flexible to enable control and operation in and by the GF sheath 640, yet are sufficiently rigid to enable extravascular penetration, snaring and/or grasping of the target arterial wall. In one specific configuration, for example, the distal end of the garage tube may be fabricated from a material having shape memory properties where, in use, the combined subsystem would cooperate the GF sheath 640 to operate and control the use of the tissue engaging device 400.

The two or more tongs 402 of the tissue engaging device 400 are configured and oriented for sliding reciprocal cooperation with an interior wall 642 of the sheath 640 to control movement and operation of the engaging device between the tissue engaging condition (FIGS. 8D, 8E) and the closing condition (FIGS. 8F, 8G). More specifically, the distal tips 404 of each tong 402, in the tissue engaging condition, will be manipulated to snare and/or engage the arterial walls 620', 620" being held taut by the tissue locator portion 202, in the expanded condition. Preferably, the engaging device distal tips 404 will be radially expanded or oriented at least as wide as the first diameter, relative to longitudinal axes 216, 350, of the closure element seated about the carrier seat 302. More preferably, the distal tips 404 will be radially expanded to a disposition greater than and beyond the first diameter to ensure sufficient snaring and/or engaging of the arterial walls surrounding the vessel opening 610. Accordingly, the tongs of the tissue engaging device are biased and/or have a disposition extending radially outward. Hence, by retracting the restrictive sheath 640 proximally relative to the garage tube 330 (or advancing the delivery assembly distally past the distal end of the sheath), the respective tongs 402 of the tissue engaging device 400 will be released and permitted to radially expand to the tissue engaging position (FIG. 8D).

Briefly, as will be described in greater detail below, once the arterial walls 620', 620" are snared or pierced by the tissue engaging device 400, in the tissue engaging condition, the GF sheath can be displaced distally, relative to the garage tube. Sliding contact between the interior wall 642 of the sheath and the outer facing surfaces 406 of the tongs 402 causes the distal tips of the engaging device to draw the tissue radially inward toward one another (FIG. 8F). As the interior wall 642 of the sheath is advanced distally, the increasing contact along the outer surfaces 406 of the tongs causes the distal tips to invert inwardly within the first diameter of the closure element in the substantially tubular configuration about the carrier seat 302, in the closing condition.

FIG. 6 best illustrates that the clip applier apparatus 100 includes a housing/handle 380 at a proximal end thereof suitable for gripping and manual support, manipulation and operation of the device and components thereof Preferably, the housing 380 is an elongated member having a proximal end 380a and a distal end 380b with a longitudinal axis 386. When the apparatus 100 is properly assembled, the tube set 305 of the delivery assembly 200 is at least partially disposed within the housing handle such that the pusher member 320 and the cover member 330 are slidable relative to the housing 380, the tubular body 210, the carrier seat 302 and the distal locator portion 202 thereof Further, respective distal end regions 210b, 320b and 330b extend from the distal end region 380b of the housing 380 such that the common longitudinal axis 350 (shown in FIG. 5A) of the tube set 305 is substantially axially aligned with the longitudinal axis 386 of the housing 380. Being configured to slidably retain the respective proximal end regions 210a, 320a and 330a, the housing 380 supports the tube set 305 and can have one or more handles 390 to facilitate use of the apparatus 100. The handles 390 extend substantially radially from the outer periphery 382 of the housing 380 and can be provided in the manner known in the art.

The present invention incorporates various switching systems, triggering systems, locking systems, etc. contained in the handle portion to effect use and operation of the delivery components described herein. While all these subsystems are not shown and described herein in detail, it will be appreciated that they are similar to the design and operation of the analogous subsystems shown and described in our '214 patent application, which as mentioned is incorporated by reference herein for all purposes.

By way of example, however, the locator portion 202 also can include a locator control system 240 that is coupled with the proximal end region 210a of the delivery assembly 200 and that is configured to selectively control the distal locator portion 202 between the unexpanded and expanded states (FIG. 4C). The locator control system 240 can selectively control the distal locator portion 202 between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210a of the tubular body 210 and the distal locator portion 202. The control member 250 has a proximal end region 250a that is coupled with the locator control system 240, preferably through a control block (not shown, but operationally similar to the control systems and structures), and a distal end section (not shown) of the control member 250 that is coupled with the expansion elements 230, and/or the movable end regions 230c' of the substantially flexible members 230'. The locator control system 240 can selectively transition the expansion elements 230, and/or the substantially flexible members 230' of the distal locator portion 202 between the unexpanded and expanded states by moving the control member 250 axially relative to the tubular body 210.

The locator control system 240 preferably includes a locator release system (not shown, but one embodiment which may be similar to that disclosed in the '214 patent application) for maintaining the unexpanded state and/or the expanded state of the distal end region 210b, the expansion elements 230, and/or the substantially flexible members 230'. The locator release system is preferably configured to maintain the locator portion in the expanded state. Any type of locking system can be employed, and can be engaged, for instance, by activating the switching system. For example, once the substantially flexible members 230' have entered the expanded state, the locator release system can secure the control member 250 to prevent axial movement relative to the tubular body 210, thereby maintaining the substantially flexible members 230' in the expanded state.

The locator control system 240 also can be configured to disengage the locator release system, such that the distal end region 210b, the expansion elements 230, and/or the substantially flexible members 230' can transition between the unexpanded and expanded states. The locator release system can be disengaged, for example, by activating an emergency release system (not shown). As desired, the locator control system 240 can further include a biasing system (not shown), such as one or more springs, to bias the distal end region 210b, the expansion elements 230, and/or the substantially flexible members 230' to enter and/or maintain the unexpanded state when the locator release system is disengaged.

In use, the closure element 500" is carried on the carrier seat 302, in the slightly radially expanded tubular configuration, and is disposed within the cover member 330. As shown in FIGS. 7A-7C, for example, the closure element 500' can be slidably received over the distal locator portion 202 and the distal end region of the carrier assembly 300. The closure element 500" is then seated and disposed about the periphery of the carrier seat 302 adjacent to the space 360, in the slightly expanded, substantially tubular configuration.

After being received over the distal end region 302b, the substantially tubular closure element 500" is disposed in the space 360, and the tines 520 are directed substantially distally as shown in FIG. 7B. To improve the engagement between the closure element 500" (shown in FIGS. 3A-3B) and the blood vessel wall 620 and/or tissue 630 (collectively shown in FIG. 8A), the substantially tubular closure element 500" preferably is disposed on the carrier seat 302 such that the tines 520 are contained in a plane.

Once disposed in the space 360, the resiliency of the slightly expanded closure element 500" and/or the addition of an adhesive or glue will facilitate retention of the element in place about the carrier seat. Moreover, the sliding receipt of the substantially tubular closure element 500" and the distal end region 320b of the pusher member 320 within the lumen 334 of the cover member 330, as illustrated in FIGS. 7B and 7C, also cooperate to retain the closure element 500" against the carrier seat 302. When the cover member 330 is properly positioned over the carrier assembly 300, the distal end region 330b (opposite of the proximal end region 330a) of the cover member 330 extends over the space 360 and defines the annular cavity for retaining the substantially tubular closure element 500". As such, the closure element 500" is disposed substantially between the outer periphery of the carrier seat 302 and the inner periphery 332a of the cover member 330 such that the substantially tubular closure element 500" maintains the substantially tubular configuration with the tines 520 being directed substantially distally. As desired, the tube set 305 may slightly radially compress the substantially tubular closure element 500" to facilitate seating against the carrier seat. The body 510 of the substantially tubular closure element 500" can be disposed distally of the distal end region 320b of the pusher member 320, as illustrated in FIG. 7C, or can engage the distal end region 320b, as desired.

Turning now to FIGS. 8A-8H, operation of this specific embodiment will now be detailed. Initially, introducer sheath 640 may be inserted or otherwise positioned through skin 650 and tissue 630 and within the blood vessel 600 or other body lumen via the opening 610. Comprising a substantially flexible or semi-rigid tubular member, the sheath 640 has a proximal end region 640a and a distal end region 640b and includes a predetermined length and a predetermined cross-section, both of which can be of any suitable dimension. The sheath 640 also forms a peripheral surface 645 and a lumen 644 that extends along a longitudinal axis of the sheath 640 and substantially between the proximal and distal end regions 640a, 640b. The lumen 644 can have any suitable internal cross-section 648b and is suitable for receiving one or more devices (not shown), such as a catheter, a guide wire, or the like. The lumen 644 is configured to slidably receive tube set 305 and the delivery assembly 200 of the apparatus 100, including the nested tubular body 210, the carrier seat 302, the distal locator portion 202, pusher member 320 and the cover member 330 as a single unit. Accordingly, one significant advantage of the present invention is that, due to the reduced complexity of the cooperating componentry, the overall diametric footprint can be significantly smaller relative to the current systems. Hence, the entire nested tube set 305 may be slidably received in the lumen 644 of the introducer sheath 640 without requiring a radial expansion or splitting of the sheath 640. Such a configuration is beneficial in that, when required, the delivery assembly 200 can be retracted and reinserted unlike the previous designs that irreversibly radially expanded, stretched, split or severed the analogous sheaths.

The introducer sheath 640 may be advanced over a guide wire or other rail (not shown) that was previously positioned through the opening 610 and into the blood vessel 600 using conventional procedures. In one specific use, the blood vessel 600 is a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, or the like, may be inserted through the sheath 640 and advanced to a predetermined location within the patient's body. For example, the devices may be used to perform a therapeutic or diagnostic procedure, such as angioplasty, atherectomy, stent implantation, and the like, within the patent's vasculature.

After the procedure is completed, the devices are removed from the sheath 640, and the apparatus 100 is prepared to be slidably received by the lumen 644 of the sheath 640 as shown in FIG. 8B. Being in the unexpanded state, the distal end region of the distal locator portion 202, via tubular body 210, is slidably received by the lumen 644 and atraumatically advanced distally into the blood vessel 600 (FIG. 8B). Briefly, it will be appreciated that, due to the fixed configuration between the distal end region of the carrier assembly 300 and the proximal end region of the distal locator portion 202, in a support configuration, that the carrier seat 302, the pusher member 320 and the cover member 330, together with the closure element in the slightly expanded, substantially tubular configuration, are also advanced distally near the blood vessel 600 as a unit. Moreover, since the pusher member 320 and the cover member 330 are also coupled to the tubular body 210, those components are likewise advanced distally together with the locator portion 202. Once the distal end region of the distal locator portion 202 extends into the blood vessel 600, the distal locator portion 202 can transition from the unexpanded state (FIG. 8B) to the expanded state (FIG. 8C) by activating the switching system of the locator portion 202.

Turning now to FIG. 8D, the apparatus 100 and the sheath 640 then are retracted proximally until the distal end region of the locator portion 202 is substantially adjacent to an inner surface 620b of the blood vessel wall 620. The distal end region of the locator portion 202 thereby draws the opposing blood vessel walls 620', 620" taut and maintains the proper position of the apparatus 100 as the blood vessel 600 pulsates. Since the expanded cross-section of the expansion elements 230 is collectively greater than or substantially equal to the cross-section of the opening 610 and/or the cross-section of the lumen 644, the expansion elements remain in the blood vessel 600 and engage the inner surface 620b of the blood vessel wall 620. The expansion elements 230 can frictionally engage the inner surface 620b of the blood vessel wall 620, thereby securing the apparatus 100 to the blood vessel 600. The sheath 640 is then retracted proximally such that the distal end region 640b of the sheath 640 is substantially withdrawn from the blood vessel 600, as shown in FIG. 8D, permitting the apparatus 100 to access the blood vessel wall 620.

While the relative distance between the distal end region of the carrier assembly 300 (i.e., the carrier seat 302) and the proximal end region of the distal locator portion 202 is preferably substantially fixed, it will be appreciated that such relative distances can be non-fixed as well. More particularly, upon establishing a first position of FIG. 8D, the carrier seat 302 and the loaded closure element 500", in the substantially tubular configuration, are disposed proximal and substantially adjacent to the outer surface 620a of the blood vessel wall 620. In this manner, the blood vessel wall 620, adjacent to the opening 610, is disposed substantially between the expanded distal region of the locator portion 202 and the distal end region of the carrier assembly 300.

Hence, once the distal end region of the locator portion 202 properly engages the inner surface 620b of the blood vessel wall 620 as the expansion elements 230 are selectively positioned and moved to the expanded state, the sheath 640 is further retracted proximally, exposing the tongs 402 of the tissue engaging device 400. As mentioned, the interior walls 642 of the sheath 640 cooperate with the garage tube 330 to maintain a substantially cylindrical profile, and to control and operate the use tongs 402 of the distal tissue engaging device, which are substantially distally facing and flush against the tubular body 210 when contained in the sheath 640. Further proximal retraction of the sheath 640 exposes the tongs 402 of the tissue engaging device 400 from inside the sheath lumen 644, allowing the distal tips 404 of the tongs to radially expand toward the engaging condition.

Depending upon the particular design of the tissue engaging device 400, movement of the distal tips 404 of the tongs may occur in different ways. For instance, if the tissue engaging device 400 is composed of a shape memory material, exposure of the heat set tissue engaging device 400 to the tissue environment causes radial expansion of the tongs 402 toward the engaging condition. In contrast, in a resilient, elbowed-type configuration of the engaging device tongs 402, as shown in FIG. 8B-8E, proximal retraction of the reduces the compressive contact of the exterior facing surfaces of the engaging device tongs 402 with the interior wall 642 of the sheath 640. This allows the distal tips 404 of the tongs to radially expand toward the engaging condition.

Once the tissue engaging device 400 has radially expanded to the tissue engaging condition, the garage tube 330 can be axially advanced distally, relative to the carrier assembly 300 and the tissue locator portion 202, maintaining the closure element 500" seated in the carrier seat 302 (not shown). It will be appreciated, however, that the tube set 305, with the exception of the tubular body 210, can be axially advanced along the tubular body together as a unit, as best viewed in FIG. 8E. Hence, as the cover member is advanced distally, so is the pusher member 320 that unseats the closure element 500" from the carrier seat 302 about the tubular body 210. Consequently, the distal tips 404 of the tongs, oriented distally toward arterial walls 620', 620" that define the vessel opening 610, are extravascularly advanced into piercing or snaring contact therewith. In cooperation with the expansion elements 230 of the distal locator portion 202, in the expanded condition, the arterial walls are maintained taut to facilitate engagement by the tongs.

Referring now to FIG. 8F, the tissue engaging device 400 at the distal end of the garage tube 330 is collapsed together in the closing condition. This is performed by sliding the sheath 640 distally, relative to the carrier assembly 300 and the tissue locator portion 202 (or retracting the garage tube 330 into the sheath 640), increasing contact and engagement of the tongs 402 with the lumen interior wall 642 of the sheath. In effect, the sliding contact pinches the distal tips 404 of the tissue engaging device tongs 402 together, pulling the opposed arterial walls 620', 620" radially inward toward the closing condition (i.e., within the first diameter of the closure element).

During operation of the tissue engaging device from the tissue engaging condition to the closing condition, the substantially tubular closure element 500" is advantageously retained on the outer periphery of the carrier seat 302 by the cover member 330 as illustrated in FIG. 8E. By retaining at least the proximal portion of the substantially tubular closure element 500" between the distal end region (e.g., the radially, inwardly directed longitudinal extensions 335) of the cover member 330 and the distal end region of the carrier seat 302, the apparatus 100 is configured to provide better tissue penetration for the seated closure element 500".

As mentioned, in one specific embodiment, the carrier seat 302 and the cover member 330 of the carrier assembly 300 cooperate to maintain the substantially tubular closure element 500" in the tubular configuration, and fixed relative to the distal tissue engaging device 400. After the tissue engaging device 400 engages the opposed arterial walls 620', 620" in the closing condition (FIG. 8F), the locator release system (not shown) can be activated to transition the expansion elements 230 of the tissue locator portion or obturator 202 from the expanded state to the unexpanded state, as shown in FIG. 8G.

The proximal end region of the locator portion 202 can be retracted proximally, effectively retracting the tubular body 210 and the distal locator portion 202 into the lumen 324 of the pusher member 320, and relative to the garage tube 330, closure element 500" and sheath 640 (FIG. 8G). Simultaneously, the distal end of the pusher member 320 can be advanced distally, contacting the closure element 500" and advancing it distally and axially along the tubular body 210 of the delivery assembly 100 and toward the tissue locator portion 202. Once the distal end region of the tissue locator portion 202 is axially proximate to the closure element 500" (e.g., seated about the expansion elements 230 of the tissue locator portion), the closure element is nearly ready to be deployed. The tissue locator portion 202 and the cover member 330 preferably are inhibited from further relative axial movement and remain substantially stationary, relative the handle portion; whereas, the pusher member 320 remains axially slidable. As the pusher member 320 selectively continues distally, the distal end region 320b of the pusher member 320 further engages the substantially tubular closure element 500" and displaces it from its seating about the expansion elements 230 of the obturator (FIG. 8G).

In accordance with the present invention, the closure element 500", seated about the delivery assembly 200 in the slightly expanded, substantially tubular condition, is delivered into engagement with the opposed blood vessel arterial wall 620', 620" and/or tissue 630 adjacent to the opening 610 without further radial expansion thereof As previously indicated, this benefit is due to the fact that the tissue engaging device 400 is simultaneously engaged with the vessel wall 620, and draws the opposed engaged sides walls 620', 620" radially inward relative to one another and within the first diameter of the closure element.

Upon being advanced over the distal locator portion 202, in the unexpanded state, by the pusher member 320, the substantially tubular closure element 500" is distally deployed as illustrated in FIG. 8G. Continued distal advancement of the pusher member 320 past the distal end of the obturator delivers the tongs 402 of the closure element 500" into piercing engagement with the arterial walls 620', 620" surrounding the vessel opening. When the substantially tubular closure element 500" is deployed, the tines 520 can pierce and otherwise engage significant amount of the blood vessel wall 620 and/or tissue 630 adjacent to the opening 610 without requiring significant further radio expansion in order to sufficiently engage the walls. Due to the simultaneous engagement of the tissue engaging device 400 with the vessel walls, the tines 520 can engage significant amount of the opposed blood vessel arterial walls 620', 620" and/or tissue 630 because the vessel walls 620', 620" are pulled together by the engaging device, in the closing condition. In particular, the tongs 402 of the tissue engaging device 400 engage the opposed vessel walls 620', 620", and urge them radially inwardly, within the first diameter (and hence within the cross-section 530) of the substantially tubular closure element 500" simultaneously while the pusher member 320 is deploying the closure element.

Once the substantially tubular closure element 500" is deployed (FIG. 8H), it begins to transition from the tubular configuration to the natural, planar configuration with opposing tines 520 and a natural cross-section 530 of the closure element 500". Preferably, the substantially tubular closure element 500" substantially uniformly transitions from the tubular configuration to the natural, planar configuration. Rotating axially inwardly to form the opposing tines 520 of the closure element 500", the tines 520 draw the tissue 630 and/or opposing vessel walls 620', 620" into the channel 540 of the transitioning closure element 500". In addition, the tissue 630 is drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500 as illustrated in FIG. 8H. Subsequently, the sheath 640 and the tube set 305 of the delivery assembly 200 can be withdrawn from the tissue 630.

To reduce interference of the closure element tines 520 with the tissue engaging tongs, while the tongs are engaged with the vessel walls 620', 620" in the closing condition, the tips 404 and the tongs 402 can be configured so as to be angularly off-set (at virtually any angle resulting in non-interference) from one another (not shown) about the common longitudinal axis 350. For example, as little as about a 5 degrees angular off-set between the engaging device tongs 402 and the closure element tines 520, about the common longitudinal axis 350, will significantly reduce contact of the tines with the tongs during delivery of the closure element.

Turning now to FIGS. 9 and 10, an alternative embodiment delivery assembly 200 is illustrated wherein the tissue engaging device 400 is disposed within and deployed from a central lumen 204 of the tubular body 210. As indicated above, the primary difference between the various embodiments of the present invention is the location, implementation and execution of the tissue engaging device 400. For example, in this embodiment, the tissue engaging device 400 is configured to intravascularly engage the opposing arterial walls 620', 620", while in the previous embodiment, the tissue engaging device extravascularly engages the arterial walls.

The primary orientation and operation of the remaining components of the delivery assembly 200, however, are similar to the previously discussed embodiments. That is, the delivery assembly 200 contains a similar tube set 305 consisting of the locator portion 202 and the carrier assembly 300, the carrier assembly of which is located at the distal end of the tubular body 210, just proximal to the locator portion 202. Briefly, the carrier assembly 300 similarly consists of the carrier seat 302, the tubular pusher member 320 and a nested garage tube 330; the latter of which surrounds the former two, and all of which are coaxial with longitudinal axis 216 of the tubular body 210.

The tissue locator portion 202 includes a tubular bleed back shaft 260 distally extending from a distal end of the carrier seat 302. Preferably, both the carrier seat and the bleed back shaft 260 are integrally formed with one another on the end of the delivery assembly tubular body 210. The bleed back shaft 260 includes a bleed back port 262 that functions to locate the vessel opening 610 at puncture site in the vessel 600. This port 262 is oriented a predetermined distance from the distal end from the bleed back shaft 260. The bleed back port 262 communicates with a bleed back lumen (not shown) that longitudinally extends from the locator portion and through the tubular body 210 of the delivery assembly, although it will be appreciated that the port could also sharing a lumen with the tissue engaging device.

In accordance with this specific embodiment, the cover member or garage tube 330 similarly covers the pusher member 320, the carrier seat 302 of the carrier assembly 300, and the tubular body 210 (i.e., tube set 305). Since the tissue engaging device is not disposed at the distal end of the garage tube, the annular distal end preferably terminates just distal to the carrier seat 302, defining the annular space 360 that seats the closure element 500" in the substantially tubular configuration. In one preferred embodiment, one or more longitudinal extensions extend distally from the garage tube or cover member 330, similar to extensions 355 of FIG. 7B. Although these longitudinal extensions can extend generally in parallel with common longitudinal axis 350, the longitudinal extensions preferably are biased such that they extend substantially radially inwardly. Thereby, the longitudinal extensions can at least partially close the central lumen 334 substantially adjacent to the distal end region of the cover member 330.

Referring back to FIG. 9, in operation, the tube set 305 of the delivery assembly 200 of the clip applier apparatus 100 is advanced through the sheath lumen 644 of the sheath 640 using similar techniques to those show and described in FIGS. 8A and 8B. When the tissue locator portion 202 locates the vessel opening 610 and the bleed back shaft 260 is inserted into the body vessel 600 to the predefined depth, the bleed back port 262 communicates with fluid flow, hence locating the vessel opening 610.

Once tissue locator portion 202 is properly oriented, the tissue engaging device 400 can be distally deployed from a distal end of the tubular body 210. As shown in FIGS. 10 and 11, the tissue engaging device 400 is slidably disposed within a lumen 204 of the tubular body 210. This lumen 204 further extends through the carrier assembly 300 and the locator portion 202, terminating at an end port 264 at the distal end thereof The tissue engaging device 400 includes one or more tongs 410 having proximal end regions associated with a common control shaft (not shown) operated at the handle portion 380 of the clip applier apparatus 100. Each resilient tong 410 is naturally bowed in a U-shaped manner such that when continually distally advanced from the tubular body end port 264, each tong resiliently bows radially outwardly from common axis 216, and bows upwardly toward the interior surface 620b of the opposing arterial walls 620', 620". As the tongs 410 of the tissue engaging device are further deployed, the tips 412 (e.g., barbed tips) of the tongs 410 are configured to intravascularly pierce, snare or grab the arterial walls 620', 620" from the underside surface 620b surrounding the puncture site (i.e., in a tissue engaging condition of FIG. 9). The snaring, piercing and/or grabbing of the arterial walls could be accomplished by hooks, barbs, or similar on the ends of the tongs 410. The piercing from the underside surface, furthermore, may be accomplished by the curved shape of the tongs 410 as they exit the distal end of the bleed back shaft 260.

Accordingly, the resilient tongs 410 are sufficiently flexible for sliding reciprocal receipt in the receiving lumen 204 of the tubular body 210 of the delivery assembly 200, yet sufficiently rigid to enable piercing, snaring or grabbing of the arterial walls when engaged therewith. Such materials exhibiting these characteristics, for example, include Nitinol and stainless steel.

Once the opposing arterial walls 620', 620" are sufficiently grasped, snared or penetrated, the tubular body 210 of the delivery assembly 200 is retracted extravascularly through the receiving lumen 204 of the pusher member 320. This operation is performed while the garage tube 330, the closure element 500" and the pusher member 320 are substantially axially maintained at their position relative to the vessel opening 610 of the body vessel 600. Accordingly, the relative movement between the tubular body 210 and the pusher member 320, in turn, unseats the closure element 500" from the carrier seat 302 and advances it toward the distal end of the tubular body 210. Alone or in combination with the above tubular body retraction, the tongs 410 of the tissue engaging device 400 may also be retracted into the receiving lumen 204 of the tubular body 210. As the tubular body 210 and/or the tongs 410 are being retracted, the arterial walls 620', 620" are pulled together radially inward until they are disposed within the first diameter of the closure element 500", in a closing condition (FIG. 10). Continued retraction further urges the engaged opposing arterial walls 620', 620" radially together under the bleed back shaft and into the channel 540 defined by the substantially tubular closure element 500".

To permit the substantially tubular closure element 500" to be deployed from the annular cavity 360, the cover member 330 can also be slidably retracted, relative the tubular body 210. The longitudinal extensions 335 of the cover member 330 preferably are sufficiently flexible to expand radially to permit retroactive movement of the distal end region of the cover member 330 peripherally over the mounted closure element 500". This opens the annular cavity 360 such that the distal end region of the cover member 330 no longer fully encloses the closure element.

Turning now to FIG. 11, the pusher member 320 is then advanced distally to deploy the closure element 500". Similar to the technique applied above, the tines 520 of the closure element 500" pierce the opposing arterial walls 620', 620" that are radially pulled together, via the tissue engaging device 400 in the closing condition, within the first diameter. Once the substantially tubular closure element 500" is deployed, it begins to transition from the tubular configuration to the natural, planar configuration with opposing tines 520 and a natural cross-section 530 of the closure element 500 (substantially similar to the deployment of the closure element detailed and shown in FIGS. 8G and 8H). The arterial walls 620', 620" are drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500, as illustrated in FIG. 8H. Subsequently, the tongs 410 of the tissue engaging device 400 are retracted in the bleed back shaft 260, and the delivery assembly 200 and sheath 640 can be removed.

It will be appreciated that the bleed back shaft 260 is composed of a material that reduces sticking of the tines 520 of the closure element during deployment, should any contact ensue. This would be detrimental, of course to the proper clip deployment. Essentially, the composition should be at least as hard as the tines of the closure element so as not to stick into the bleed back shaft itself. Beneficial shaft compositions include any hard material that can be formed into a tube and is also biocompatible, such as stainless steel and Nitinol to name a few. Further, similar to the embodiments above-mentioned, the seating of the closure element 500" about the carrier seat 302 is in a manner angularly off-setting the closure element tines 520 (relative to the longitudinal axis 216) from the angular position of the tissue engaging tongs 410, to reduce interference during deployment of the closure element.

FIGS. 12 and 13 represent another specific embodiment clip applier apparatus 100 incorporating a tissue engaging device 400 that intravascularly engages the opposing arterial walls 620', 620". In accordance with this specific embodiment, however, the analogous tongs 410 cooperate to radially push the engaged opposing arterial walls together as opposed to radially pulling them together, as does the embodiment disclosed in FIGS. 9-11. As best illustrated in FIG. 12, the tongs 410 of the tissue engaging device 400, in their natural configuration, are substantially C-shaped. For each tong 410, the respective distal tip 412 is configured to loop nearly all the way around onto itself. That is, in their respective own plane substantially intersecting the longitudinal axis 216 of the bleed back shaft 260, the distal tip of each tong loops back around from the end port 264 of the bleed back shaft 260. Briefly, it will be appreciated that natural loop shape of each tong neither needs to be exactly circular, nor be curvilinear for that matter, as long as the tip 412 extends back around in a direction toward the longitudinal axis 216 of the shaft 260.

Again, using similar placement and advancement techniques through the sheath lumen 644 of the sheath 640, as show and described in FIGS. 8A and 8B, the tube set 305 of the delivery assembly 200 can be positioned near the vessel opening 610. Once the tissue locator portion 202, via bleed back port 262, has determined the location and proper depth of insertion of the bleed back shaft 260 into the vessel opening 610 of the vessel body 600, the two or more tongs 410 are advanced distally out of the shaft end port 264, via controls at the handle member 380 (FIG. 6). As the advancement of the tongs 410 of the tissue engaging device 400 distally continue, the tips 412 of the tongs 410 continue to loop back around until they grip, snag and/or partially pierce the underside surface 620b the in opposing arterial walls 620', 620" (in a manner similarly described in the operation of the embodiment of FIGS. 9 and 10).

Once the arterial walls 620', 620" are sufficiently initially engaged, further advancement of the tongs from the distal end port 264 of the bleed back shaft 260 causes the tong tips 412 to return to their natural state, in their respective plane (i.e., directed back toward longitudinal axis 216 of the bleed back shaft 260). In effect, the engaged opposed arterial walls 620', 620" are pushed together by the advancing tong tips 412, which return to their natural state, until the edges 622', 622" of the opposing arterial walls 620', 620" contact the exterior surface of the bleed back shaft 260. Accordingly, unlike the previous embodiment, the engaged opposing arterial walls 620', 620" are urged together without retracting the bleed back shaft 260 and/or retracting the tongs 410 back into the receiving lumen 204. This is beneficial in that it allows the user to continue monitoring the proper location of the device. Further, by not retracting the tongs, the chance that the tongs dislodge from the arterial walls decreases prior to deployment of the closure element.

Accordingly, the tips 412 of the respective tongs 410 are configured to not fully penetrate the engaged opposing arterial wall 620', 620" or each tong may experience difficulty urging and pushing the opposing walls back toward and against the bleed back shaft. For example, the tip configuration can be more blunted, radiused or roughened, so as to partially pierce the tissue, but not fully penetrate it.

Regarding the resilient tongs 410, they must be capable of sufficient flexibility to unfold from their naturally curved and hooked configuration to a substantially straight configuration when housed or stored within the lumen 204 of the tubular body 210. However, the tongs 410 of the tissue engaging device 400 must also be sufficiently stiff, strong and resilient to push the engaged arterial walls together, and back against the bleed back shaft 260 when the tongs are fully deployed from the distal end of the bleed back shaft 260. Such materials for each tong 410, for example, may include Nitinol and stainless steel.

Since the opposed arterial walls 620', 620" must be pushed, as opposed to pulled, radially together to an orientation within the first diameter of the seated closure element 500", the diameter of the bleed back shaft 260 at the region of contact by the edge 622', 622" of the arterial walls 620', 620" is reduced from that of the carrier seat 302. Such a diameter reduction, relative to the carrier seat, increases the width of tissue engagement about by the tines 520 of the closure element 500", about the vessel opening 610, by enabling the opposed arterial walls to be pushed closer together.

Referring now to FIG. 14, the pusher member 320 may be distally advanced to engage the seated closure element 500", in the substantially tubular condition, during deployment. The delivery assembly 200, and hence the bleed back shaft 260, are axially maintained in position during the deployment of the closure element 500". Once the substantially tubular closure element 500" is deployed, it begins to transition from the tubular configuration to the natural, planar configuration with opposing tines 520 and a natural cross-section 530 of the closure element 500 (substantially similar to the deployment of the closure element detailed and shown in FIGS. 8G and 8H). Again, the opening 610 in the blood vessel wall 620 can be drawn substantially closed and/or sealed via the closure element 500" as illustrated in FIG. 8H. Subsequently, the tongs 410 of the tissue engaging device 400 are the retracted in the bleed back shaft 260, and then the bleed back shaft 260 is retracted from the "closed" opening 610 of the puncture site.

It will again be appreciated that the bleed back shaft 260 is composed of a material that reduces sticking of the tines 520 of the closure element therewith during deployment and withdrawal of the shaft from the opening, should any contact ensue. As mentioned above, beneficial shaft compositions include any hard material that can be formed into a tube and is also biocompatible, such as Nitinol and Stainless steel. Furthermore, the seating of the closure element 500" about the carrier seat 302 is in a manner angularly off-setting the closure element tines 520 (relative to the longitudinal axis 216) from the angular position of the tissue engaging tongs 410, to reduce interference during deployment of the closure element.

Referring now to FIG. 15, another specific embodiment of the clip applier apparatus 100 is illustrated that is structurally and functionally similar to the clip applier apparatus embodiment detailed in FIGS. 9-11. In this specific embodiment, however, the cover member or garage tube 330 shown in the embodiment of FIG. 9 is removed, providing a significantly reduced diametric footprint for the tube set 305 of the delivery assembly 200. Accordingly, during advancement of the delivery assembly to the vessel opening 610, via the lumen 644 of the sheath 640, protection of the seated closure element 500" is afforded by the sheath itself.

As above-mentioned, the diametric footprint of the clip applier apparatus 100 in this specific embodiment is further reduced by an amount equivalent to the removal of the garage tube from the tube set 305. Hence, the tube set 305 of the delivery assembly only includes the pusher member 320 of the carrier assembly 300, and the tubular body 210. The tubular body 210, which supports the carrier seat 302, the tissue locator assembly 202 and the tissue engaging device 400 supported within the receiving tubular body lumen 204, may similarly be capable of axial displacement, relative to the sheath 640, the pusher member 320 and the closure element 500", in the substantially tubular configuration.

Furthermore, the introducer sheath 640 will selected to cooperate with the tube set 305 of the delivery assembly 200 in a manner similar to the cooperation between the garage tube 330 and the pusher member 302 and closure element 500" of the previous embodiments. That is, the interior diameter of the sheath lumen 644 should be sized to cooperate with the exterior diameter of the pusher member 320 and the seated closure element 500" to permit sliding axial displacement therebetween, yet be sufficiently snug at the distal tip to retain the closure element in the substantially tubular configuration until it is released out of its distal thereof.

Referring back to FIG. 15, the tissue engaging device 400 of this embodiment is illustrated incorporating a similar device to that described in the embodiment of FIGS. 9-11 (i.e., centrally deployed resilient tongs 410). It will be appreciated, however, that any tissue engaging device could be incorporated that is functionally capable of engaging and urging the opposed arterial walls 620', 620" together and radially within the first diameter of the closure element 500" (about longitudinal axis 216).

Again, similar to the operation of the embodiment of FIGS. 9-11, once the tissue locator portion 202 is properly oriented, the tissue engaging device 400 can be distally deployed from a distal end of the tubular body 210. The tissue engaging device 400 includes one or more tongs 410 having proximal end regions associated with a common control shaft (not shown) operated at the handle portion of the clip applier apparatus 100. Each resilient tong 410 is naturally bowed in a U-shaped manner such that when continually distally advanced from the tubular body end port 264, each tong resiliently bows radially outwardly from common axis 216, and bows upwardly toward the interior surface 620b of the opposing arterial walls 620', 620". Once the tongs 410 of the tissue engaging device are sufficiently anchored to the corresponding arterial walls 620', 620" (in the tissue engaging condition similar to that shown in FIG. 9), the tubular body 210 and/or the tongs 410 are retracted, while the pusher member 320 and the closure element 500" are substantially maintained, axially. Similar to the closing condition of FIG. 10 and as shown in FIG. 15, the engaged opposing arterial walls 620', 620" are drawn and urged together, radially inward toward one another until they are disposed within the first diameter of the closure element 500". Continued retraction further urges the engaged opposing arterial walls 620', 620" radially together under the bleed back shaft and into the channel 540 defined by the substantially tubular closure element 500".

The pusher member 320 is then advanced distally to deploy the closure element 500" off of the end of the obturator or tissue locator device 202, and out of the lumen 644 of the introducer sheath 640. The distally directed tines 520 of the closure element 500" pierce the opposing arterial walls 620', 620" that are radially pulled together, via the tissue engaging device 400 in the closing condition, within the first diameter. Once the substantially tubular closure element 500" is deployed, it begins to transition from the tubular configuration to the natural, planar configuration with opposing tines 520 and a natural cross-section 530 of the closure element 500 (substantially similar to the deployment of the closure element detailed and shown in FIGS. 8G and 8H). The arterial walls 620', 620" are thus drawn substantially closed and/or sealed. Subsequently, the tongs 410 of the tissue engaging device 400 are retracted in the bleed back shaft 260, and the delivery assembly 200 and sheath 640 can be removed.

The present invention has been described using various element identifiers to represent elements in the figures. It should be considered that the element identifiers described in connection with a particular figure may be shown in a different figure for purposes of clarity. Thus, the element identifies described in connection to a particular figure may be illustrated in a different figure for clarity because the same element identifiers have been used to describe the same elements.

The invention is susceptible to various modifications, alternative forms and uses, and specific examples thereof have been shown by way of example in the drawings and are herein described in detail. For instance, while the present invention has been primarily described for use in vessel closure, it will be appreciated that the present invention may be suitable for other repair applications as well, such as for patent foramina ovalia (PFO) application. Other modifications may include a guide wire lumen so that the distal ends may be positioned over a guide wire as well. It should be understood, however, that the invention is not to be limited to the particular forms or methods disclosed, but to the contrary, the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A closure system for closing an opening formed in a body lumen perimeterically defined by opposing arterial walls, said system comprising:
   a closure element adapted to deform from a natural, substantially resilient planar configuration to a substantially tubular configuration, having a substantially natural transverse cross-sectional dimension;
   a delivery assembly positionable through said tissue and into the opening in the body lumen, and having an elongated body, a carrier assembly and a distal tissue engaging device, said carrier assembly configured to be slidably received in a lumen of an introducer sheath, said carrier assembly including a carrier seat configured to carry and peripherally support said closure element in the substantially tubular configuration, in a first diameter, and said distal tissue engaging device selectably axially displaceable relative to said carrier seat between an engaging condition, in which said distal tissue engaging device is configured to engage the opposing arterial walls of said body lumen adjacent to said opening, and a closing condition, in which said distal tissue engaging device is configured to urge the engaged opposing arterial walls substantially transversely together such that the closure element can be deployed from the carrier assembly, while substantially maintained in the first diameter, into the opposing arterial walls, said distal tissue engaging device including two or more opposed engaging tongs having respective tips, said two or more tongs being configured to resiliently move radially outwardly from a longitudinal axis of the carrier assembly to extend said respective tips outwardly beyond an outer diameter of the carrier seat, wherein the tissue engaging device is configured to cooperate with the introducer sheath to enable movement of said two or more tongs between the engaging condition, with said two or more tongs resiliently moving radially outwardly to the engaging condition, and the closing condition and the closure element being configured to be deployed between said two or more tongs; and
   a pusher member slidably disposed about said elongated body for relative axial sliding displacement therebetween, said pusher member having a contact portion disposed proximally adjacent the closure element to selectively distally deploy said closure element from said carrier assembly, in the substantially tubular configuration, to engage said opposing arterial walls and to return to said natural, substantially planar configuration and said natural, transverse cross-sectional dimension such that the engaged opposing arterial walls are drawn substantially closed.

2. The apparatus of claim 1, wherein said two or more opposed engaging tongs having respective end tips are configured to open radially in directions extending beyond the outer diameter to initially engage the opposing portions of the arterial wall, in the engaging condition.

3. The apparatus of claim 1, wherein said carrier assembly having a cover member, said cover member being configured to protect at least said closure element which is contained therein.

4. The apparatus of claim 3, wherein said distal tissue engaging device is integral with a distal end of said cover member.

5. The apparatus of claim 1, wherein said carrier assembly is formed and dimensioned for sliding axial, reciprocating, receipt in a lumen of the introducer sheath extending through said tissue and terminating proximate the opening, wherein distal retraction of the introducer sheath exposes said two or more tongs to allow the tips to extend to the tissue engaging position and distal sliding of the introducer sheath moves said two or more tongs to the closing condition.

6. The apparatus of claim 1, further comprising a locator to position the carrier assembly and distal tissue engaging device adjacent to the opening in the body lumen, the locator having a distal locator portion selectably controllable between an unexpanded state and an expanded state for engaging the opposing portions of the arterial wall of said body lumen.

7. The apparatus of claim 1, further including a distal tissue locator portion contained on said delivery assembly, and configured to facilitate detection of the body lumen, said distal locator portion including one or more expansion elements configured to expand substantially transversely with respect to a longitudinal axis of the distal locator portion.

8. The apparatus of claim 7, wherein said distal locator portion is selectably controllable between an unexpanded state and an expanded state for engaging said opposing arterial walls of said body lumen.

9. The apparatus of claim 8 wherein in said unexpanded state, said distal locator portion has a transverse cross-sectional dimension less than that of said opening, and in said expanded state, said distal locator portion has a transverse cross-sectional dimension greater than or substantially equal to that of said opening.

10. The closure system of claim 1, wherein said pusher member comprises one or more distally extending longitudinal extensions.

11. The closure system of claim 1, further comprising a locator slidably receivable within said pusher member and said delivery assembly.

* * * * *